United States Patent
Savarino et al.

(10) Patent No.: US 8,785,493 B2
(45) Date of Patent: Jul. 22, 2014

(54) TREATMENT OF RETROVIRAL RESERVOIRS EXPLOITING OXIDATIVE STRESS

(75) Inventors: Andrea Savarino, Rome (IT); Antonello Mai, Rome (IT); Anna Teresa Palamara, Rome (IT); Enrico Garaci, Rome (IT)

(73) Assignee: Istituto Superiore di Sanita, Rome (IT)

( * ) Notice: Subject to any disclaimer, the term of this patent is extended or adjusted under 35 U.S.C. 154(b) by 163 days.

(21) Appl. No.: 13/125,325

(22) PCT Filed: Oct. 29, 2009

(86) PCT No.: PCT/EP2009/007958
§ 371 (c)(1),
(2), (4) Date: Sep. 2, 2011

(87) PCT Pub. No.: WO2010/049182
PCT Pub. Date: May 6, 2010

(65) Prior Publication Data
US 2011/0305774 A1    Dec. 15, 2011

(30) Foreign Application Priority Data

Oct. 29, 2008  (GB) .................................. 0819857.4
May 22, 2009  (GB) .................................. 0908952.5

(51) Int. Cl.
*A61K 31/28*   (2006.01)
*A61K 31/70*   (2006.01)
*A61K 33/24*   (2006.01)

(52) U.S. Cl.
USPC ................ 514/495; 424/649; 514/23; 514/25

(58) Field of Classification Search
None
See application file for complete search history.

(56) References Cited

PUBLICATIONS

Hamer, DH. "Can HIV be Cured? Mechanisms of HIV Persistence and Strategies to Combat it" Current HIV Research, (2004), vol. 2, pp. 99-111.*

Legrand-Poels et al. "Activation of Human Immunodeficiency Virus Type 1 by Oxodative Stress" AIDS Research and Human Retroviruses (1990), vol. 6, No. 12, pp. 1389-1397.*
Rigobello et al. "Effect of Auronofin on the mitochondrial generation of hydrogen peroxide. Role of thioredoxin reductase" Free Radical Research (2005), vol. 39, No. 7, pp. 687-695.*
Lu et al. "Targeting thioredoxin reductase is a basis for cancer therapy by arsenic trioxide" PNAS (Jul. 24, 2007), vol. 104, No. 30, pp. 12288-12293.*
Demonte et al. "Administration of HDAC inhibitors to reactivate HIV-1 expression in latent cellular reservoirs: implications for the development of therapeutic strategies" Biochemical Pharmacology, (2004), vol. 68, Issue 6, pp. 1231-1238.*
Interview with Professor Luc Montagnier, dated Jun. 25, 2002, available on the World Wide Web at address: http://www.anti-oxidant-enzyme.com/montagnier.html (last accessed Aug. 22, 2013) ("Montagnier Interview").
Jeon KI et al., J Immunol. Jun. 1, 2000; 164(11):5981-9.Feb; 55(2):245-51.
Piedimonte G. et al., J Infect Dis. Sep. 1997; 176(3):655-64.
Premanathan M. et al., AIDS Res Hum Retroviruses. Mar. 1, 1997; 13(4):283-90.
Sappey C. et al., Arch Biochem Biophys. Aug. 1, 1995; 321(1):263-70.
Simon G. et al., Chem Biol Interact. Jun. 1994; 91(2-3):217-24.
Yamashita M. et al., J Pharm Pharmacol. 2003; 55: 245-251.

* cited by examiner

*Primary Examiner* — Abigail Fisher
*Assistant Examiner* — Daniel L Branson
(74) *Attorney, Agent, or Firm* — Fish & Richardson P.C.

(57) ABSTRACT

Activation of HIV-1 replication causes oxidative stress, which in turn potentiates HIV-1 replication. The common basis for the compounds of the present invention is: A) the capacity of reactivating HIV-1 from latency, and B) the ability to counteract the cellular machinery which activates in order to limit the effects of oxidative stress. In this way, oxidative stress can be potentiated and a "chain reaction" is sparked. This "chain reaction" induces a more efficient reactivation of HIV-1 from latency and, in some cases, induces selective killing of the infected cells. Actions A) and B) can either be carried out by one drug exerting both effects, or obtained by the combined use of distinct drugs. There are two main cellular machineries counteracting oxidative stress, i.e. the thioredoxin (Trx) thioredoxin reductase (TrxR) system and glutathione. Herein, we present drug strategies capable of exerting action B) by blocking either of the two machineries.

8 Claims, 12 Drawing Sheets

TREATMENT OF RETROVIRAL RESERVOIRS EXPLOITING OXIDATIVE STRESS

Figure 1:
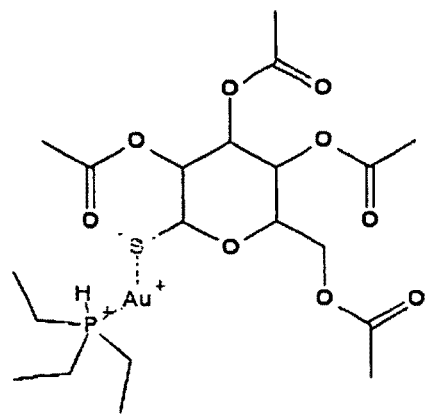

This is the U.S. national phase of International Patent Application No. PCT/EP2009/007958 filed on Oct. 29, 2009, which published on May 6, 2010 as International Publication No. WO 2010/049182. The International application also claims priority to application nos. 0819857.4 and 0908952.5 filed in the United Kingdom on Oct. 29, 2008 and May 22, 2009, respectively.

The present application relates to the use of certain compounds or combinations of compounds in the treatment of latent viral reservoirs, particularly HIV-1. Treatment of the viral reservoirs is by the exploitation of oxidative stress: A drug repositioning approach. The compounds include gold-containing compounds, such as auranofin, arsenic-containing compounds, such as arsenic trioxide, and HDAC inhibitors in combination with BSO.

INTRODUCTION TO THE INVENTION

Eradication of HIV-1 infection from the body has encountered exceptional difficulties in the presence of the latent viral reservoir, represented mainly by memory $CD4^+$ T-lymphocytes, which can neither be targeted by current antiretroviral therapies (ART) nor recognised by the immune system. For this purpose, so-called "shock and kill" strategies have been proposed [Hamer, 2004], based on a) stimulation of viral antigen expression in latently infected cells (i.e., the "shock" phase) in the presence of intensified ART to suppress viral spread due to virus expression, and b) killing of latently infected cells by the immune system or other means (i.e., the "kill" phase). For each of these phases, effective drugs are being extensively searched for.

Classical drug discovery involves target discovery and validation, lead identification by high-throughput screening, and lead optimization by medicinal chemistry. An alternative drug development strategy is the exploitation of established drugs that have already been approved for treatment of non-infectious diseases and whose targets are particularly interesting for the disease whose cure is being searched for [Dueñas-González et al., 2008]. This strategy is also denominated drug repositioning, or indication switch [Dueñas-González et al., 2008]. One successful example of drug repositioning is furnished by chloroquine. In addition to its use in the antimalarial arsenal, chloroquine has been utilized for treatment of autoimmune diseases such as rheumatoid arthritis, and is now in clinical trials as a potential agent for treatment of certain types of cancer and viral infections [Savarino et al., 2006; Savarino et al., 2007].

For the "shock" phase of HIV-1 eradication strategies, histone deacetylase inhibitors (HDACIs), currently in clinical trials as anticancer agents, have been proposed [Demonté et al., 2004; Mai et al., 2009]. Unfortunately, the effects of currently available compounds on HIV-1 activation from quiescence are associated with toxicity [Duverger et al., 2009]. New HDACIs), which are epigenetic drugs inducing HIV-1 escape from latency, which be class and isoform specific, have recently been discovered [Mai et al., 2009]. These compounds specifically inhibit those histone deacetylases (HDACs) belonging to the class I grouping, which are specifically involved in maintaining HIV-1 latency. However, toxicity remains a major concern. Moreover, similarly to the non-class-specific HDAC is of former generation, these drugs are not able to induce HIV-1 activation in all of the cells within a latently infected cell population. This suggests that there are different chromatin environments maintaining HIV-1 latency in different cells. Therefore, diverse stimuli will be required to efficiently purge HIV-1 from reservoirs.

In this regard, oxidative stress is thought to be an important area for virus/host interaction. Metal ions, and other thiol-reactive chemical species, may play an important role in the genesis of oxidative stress. Iron, a metal ion shown to generate hydroxyl radicals through the Fenton reaction, was found to be increased in productively HIV-1-infected cells and to promote HIV-1 replication in vitro [Savarino et al., 1999]. This metal, however, is at present unlikely to find a place in HIV-1 reactivating strategies, due to the side effects and the complexities of its administration in vivo. Given the poor adsorption and biodistribution of iron carriers, this metal is unlikely to reach sufficient plasma levels for efficient HIV-1 activation from the latent reservoirs.

Metals other than iron may cause oxidative stress. One such metal is gold [Sannella et al., 2009]. Gold-containing compounds have been shown to be useful in the treatment of rheumatoid arthritis [Patai, 1999] and have been considered in anticancer strategies. Their proposed usefulness in anticancer treatments is due to their antiproliferative properties. The lead structure for antitumor-active gold complexes is auranofin (FIG. 1), which is characterized by its gold(I) central atom as well as a triethylphosphine and a carbohydrate ligand. However, auranofin has been shown to silence HIV activation, i.e. maintain latency (Jeon et al., 2000; Traber et al., 1999).

SUMMARY OF THE INVENTION

It is well known that activation of HIV-1 replication causes oxidative stress, which in turn potentiates HIV-1 replication. The common basis for the compounds of the present invention is: A) the capacity of reactivating HIV-1 from latency, and B) the ability to counteract the cellular machinery which activates in order to limit the effects of oxidative stress. In this way, oxidative stress can be potentiated and a sort of "chain reaction" is sparked. This "chain reaction" induces a more efficient reactivation of HIV-1 from latency and, in some cases, induces selective killing of the infected cells. Actions A) and B) can either be carried out by one drug exerting both effects, or obtained by the combined use of distinct drugs. There are two main cellular machineries counteracting oxidative stress, i.e. the thioredoxin (Trx) thioredoxin reductase (TrxR) system and glutathione. Herein, we present drug strategies capable of exerting action B) by blocking either of the two machineries.

We have conducted experiments to test whether, and how, auranofin might activate HIV-1 in cell line models for HIV-1 quiescence. Surprisingly, we have shown that the gold(I)-containing compound auranofin is a potent inducer of HIV-1 activation from quiescence and is thus useful in HIV-1 eradication. Auranofin shows remarkable activity in activating reservoirs of latent retrovirus. In combination with known antiretroviral therapy or treatment (ART), this may then be used in therapy to reduce or eliminate retrovirus infection. The effects of auranofin on HIV-1 reactivation are particularly surprising because this drug was believed to act in the opposite way (silence HIV), as discussed elsewhere.

Specifically, auranofin has been found to stimulate the reproduction of retroviruses from latent reservoirs (of said retroviruses), and this may be used to reduce or eliminate these reservoirs in combination with conventional antiretroviral therapy. Further, histone deacetylase inhibitors (HDA- Ci's), iron nitriloacetate and buthionine sulfoximine has each been found to substantially potentiate the capacity of auranofin to combat HIV-1 latency.

We have also surprisingly found that arsenic-containing compounds and combinations of a histone deacetylase inhibitor with a glutathione synthesis inhibitor such as buthionine sulfoximine (BSO) are also effective in treating latently infected cells. In particular, the actives are able to target and selectively kill infected, but not uninfected, cells.

Therefore, certain oxidative stress inducers are useful in the treatment of a retroviral reservoir.

Thus, in a first aspect, there is provided the use of an oxidative stress inducer in the treatment of a retroviral reservoir, wherein said oxidative stress inducer is a non-iron metallodrug, which is an epigeneitic modulator.

The inducer is a non-iron metallodrug epigeneitic modulator, for instance gold-containing compounds, such as auranofin, or arsenic-containing compounds, such as arsenic trioxide, or combinations of a histone deacetylase inhibitor with a glutathione synthesis inhibitor such as buthionine sulfoximine. Cisplatin, for instance, is a mettallodrug but does not have epigenetic properties. The oxidative stress inducer may be a pro-oxidant molecule.

The present metallodrug is a compound comprising a metal ion and having biological activity. These metallodrugs includes metals able to induce a re-arrangement of gene expression profiles within a cell. This may be exploited to induce HIV-1 activation from latency. The present metallodrugs may also have particular chemical properties. In general, it is preferred that they are able to release an ion carrying one positive charge. Optionally, they may also meet particular stearic requirements.

For example, gold(I)-containing compounds fully meet these criteria. These compounds may consist of an organic carrier and a gold(I) ion, which is released. Although this invention is not linked to any particular mechanisms, the atomic size of gold (approx. 174 pm) allows insertion in the active site of TrxR to form a complex with cysteins/selenocysteins fundamental for the biological activity of this protein. A three-dimensional structure can be seen in the Protein Data Bank (accession number: 3H4K). In this manner, the activity of TrxR is inhibited.

The active ion of the present metallodrugs may also be a non-metal ion capable of mimicking the gold(I) ion. In this context, some metalloid-containing drugs, such as arsenic trioxide ($As_2O_3$) may be considered as epigenetic metallodrugs. Arsenic trioxide releases an arsenic monoxide ion carrying one positive charge and meets the structural requirements to form covalent adducts with the cysteins or selenocystein present in reductases (atomic size of arsenic: 115 pm; atomic size of oxygen: 60 pm). A structure of arsenic oxide in complex with a Trx suoperfamily member can be seen in the Protein Data Bank (accession: 1J9B). This structure strongly suggests that one similar adduct is formed with thioredoxin reductase.

The ion released by the present metallodrug may thus not be derived from platinum, the oxidation of which can only result in Pt(II) or Opt(IV) ions, or iron, from which Fe(II) or Fe(III) ions are derived and has a shorter atomic size as compared to gold. Thus, metallodrugs comprising iron ions or platinum ions are excluded from the present invention and are considered only if combined with one of the aforementioned metallodrugs of the invention. Particularly preferred examples are compounds comprising gold, preferably gold (I), or arsenic ions. Preferred gold-containing compounds include gold salts or gold derivatives. Auranofin is particularly preferred. Preferred arsenic-containing compounds include arsenicals such as arsenic oxides, which include white arsenic ($As_2O_3$, but may also be found as $As_4O_6$). Arsenic trioxide ($As_2O_3$) is particularly preferred. Another common activity shared by gold(I)-containing compounds and arsenic trioxide is the capacity to act as superoxide dismutase mimics, thus facilitating intracellular production of radical oxygen species (ROS). ROS are largely known to activate HIV-1 from latency.

Epigeneitic modulators are known in the art to play a role in DNA methylation and chromatin remodelling, i.e. in DNA winding and/or unwinding, thereby modulating gene expression.

The non-iron metallodrug epigeneitic modulator is capable of inducing oxidative stress. It is also preferably capable of inhibiting thioredoxin reductase (TrxR) and/or acting as a superoxide dismutase (SOD) mimic. The metallodrug preferably inhibits thioredoxin reductase by to blocking its active site. This may be achieved by complexing directly with the selenocystein residue known to be important for the reducing activity of these proteins. The metallodrug may also suppress synthesis of TrxRs.

Pro-oxidant molecules are also envisaged, particularly inhibitors of gamma-glutamyl cysteine synthetase, a limiting enzyme in the glutathione synthetic pathway [Anderson, 1998]. Preferred inhibitors of this enzyme include buthionine sulfoximine (BSO), an irreversible inhibitor. BSO is thus a glutathione synthesis inhibitor and such inhibitors are also preferred. The inhibitor is most preferably provided in combination with a histone deacetylase inhibitor (HDACi).

The compounds of the present invention (which can include combinations such as a glutathione synthesis inhibitor with an HDACi) are capable of selective killing. This is the ability to target and destroy latently infected cells, but not uninfected cells. In other words, cells comprising viral reservoirs are targeted but uninfected cells are not destroyed, leading to an advantageous reduction in side effects. It is preferred that the target cells are transitional memory T-$CD4^+$ cells ($T_{TM}$s) or the central memory T $CD4^+$ cells ($T_{CM}$s). These are the principal reservoir for HIV-1 latency in individuals under antiretroviral therapy (ART) and presenting low CD4 counts [Chomont et al., 2009]. the central memory T $CD4^+$ cells ($T_{CM}$s) are precursors of $T_{CM}$s and represent a more stable HIV-1 reservoir. Thus, the present invention is particularly useful in treating patients with viral reservoirs, especially those patients who are presenting low CD4 counts. Said patients should be undergoing, or have undergone, antiretroviral therapy (ART) as this can assist in preventing the newly formed virus infecting other cells.

Also provided is a method of treating a patient suspected of having a retroviral reservoir, comprising administering to said patient an oxidative stress inducer as defined herein, which may include a non-iron metallodrug epigenetic modulator or an HDACi together with a glutathione synthesis inhibitor, such as buthionine sulfoximine. The method may further comprise administering at least one of a (further) histone deacetylase inhibitor (HDACi), BSO, gold-containing compound, such as auranofin, an arsenic-containing compound, such as arsenic trioxide ($As_2O_3$) and/or iron nitriloacetate or ferrous sulphate.

The invention also provides a method of selectively targeting cells latently infected by a retrovirus, said method comprising contacting the cells with said oxidative stress inducer.

Thus, we provide strategies capable of not only activating HIV-1 from latency, but also of counteracting the cellular antioxidant machinery maintaining HIV-1 in a quiescent state. In case of epigenetic metallodrugs, both activities are carried out by the same drug (induction of ROS activating HIV-1 replication and inhibition of the cellular antioxidant protein TrxR). In case of the HDACi plus BSO combination, these effects are exerted by separate drugs (an HDACi inducing epigenetic HIV-1 reactivation, and BSO inhibiting the synthesis of the cellular reducing peptide, glutathione).

BRIEF DESCRIPTION OF THE INVENTION

FIG. 1. The structure of auranofin [gold(1+); 3,4,5-triacetyloxy-6-(acetyloxymethyl)oxane-2-thiolate; triethylphosphanium].

Figure 2:
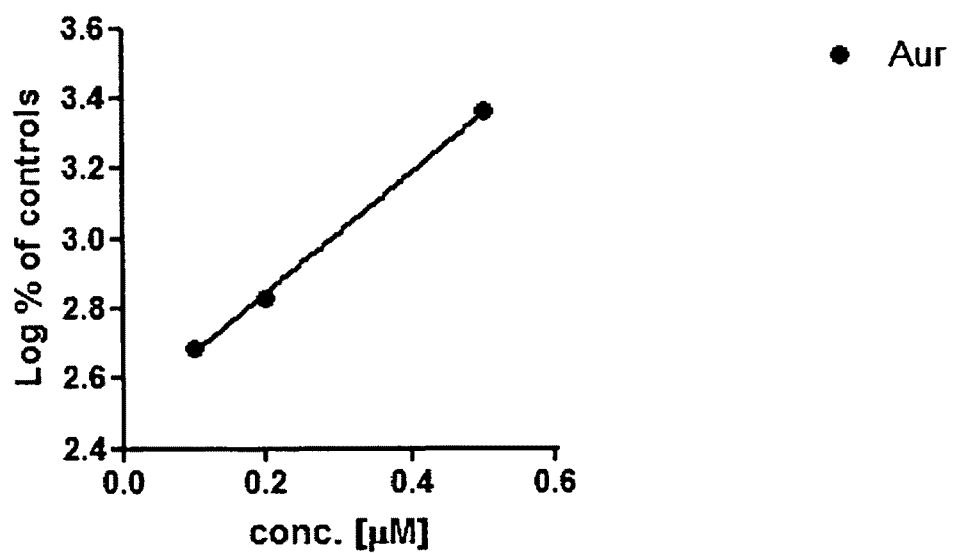

FIG. 2. Dose-dependent stimulation of HIV-1 replication by auranofin in ACH-2 cells.

The graph shows the concentration-dependent stimulation of HIV-1 p24 production in ACH-2 cells at Day 3 of incubation with the drugs. x axis: Drug concentration; y axis: fold-increase in HIV-1 p24 (Log transform of the percentage of baseline levels in untreated cultures). The line or curve best fitting the data points is shown.

Figure 3:
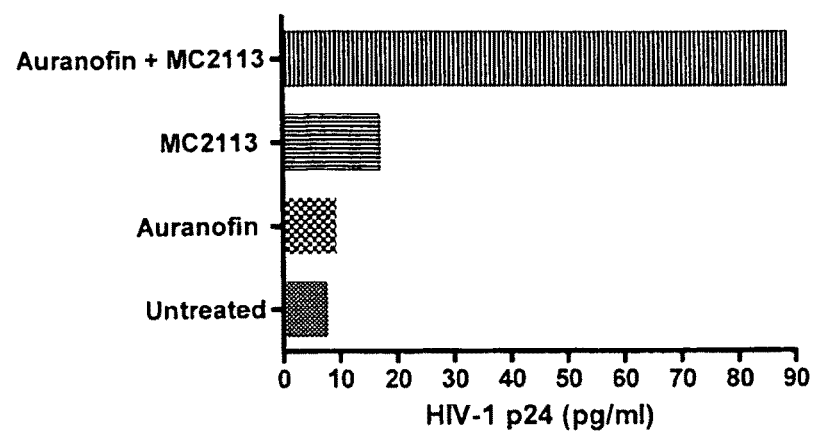

FIG. 3. Combined effects of auranofin (0.25 □M) and MC2113 (1 □M) on HIV-1 replication in U1 cells. U1 cells were incubated with either drug alone, or in combination, and p24 production was assessed at 24 h of treatment. In this case, the synergistic effect was so evident that it did not need analysis using percentage-of-synergism surfaces.

Figure 4:
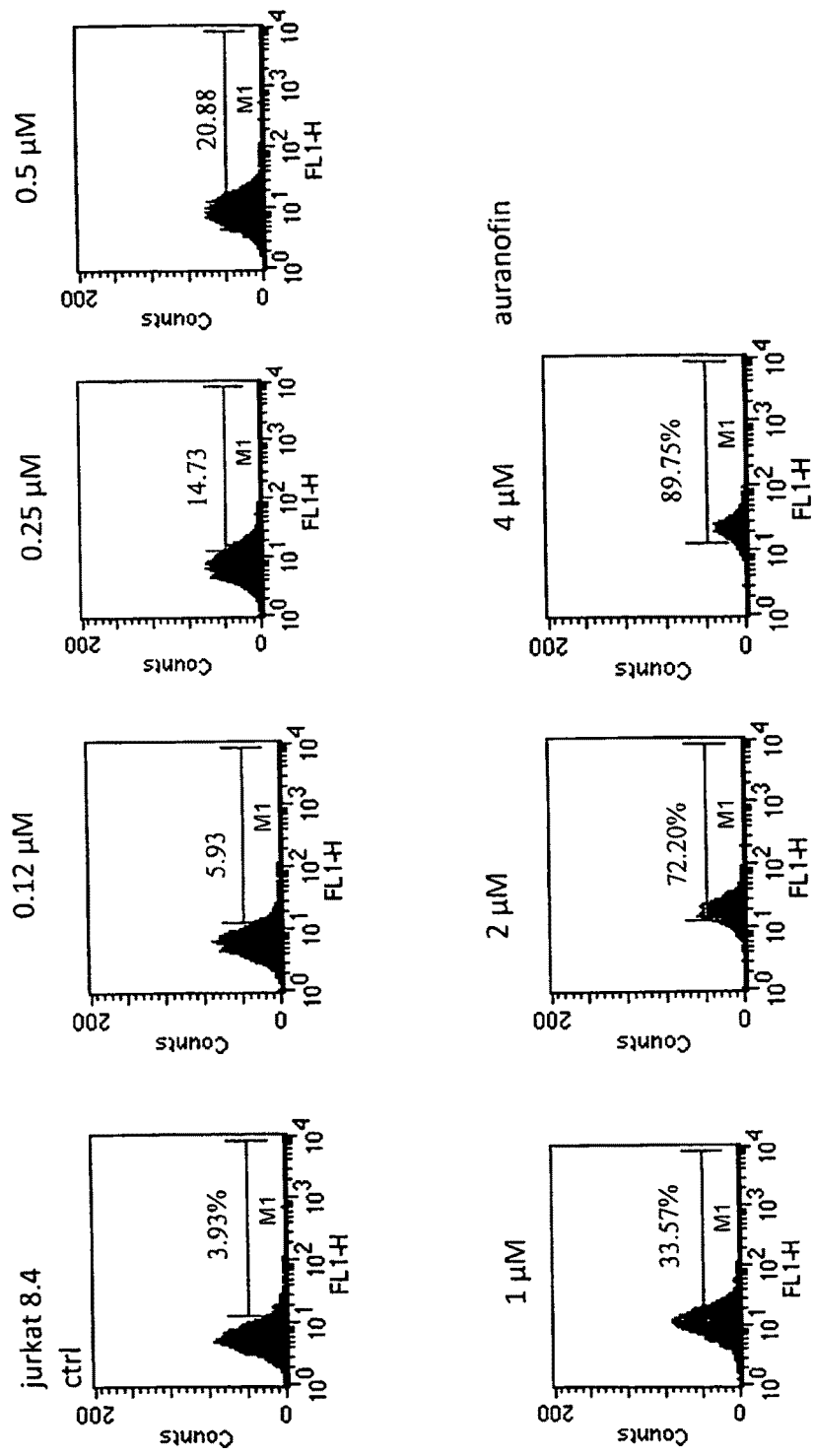

FIG. 4. Dose-dependent induction of LTR-controlled expression of green-fluorescent protein (GFP) by auranofin. We used quiescently infected T-lymphoid Jurkat cell clone, established by Jordan et al. (2003). This clone, namely 8.4, contains the entire HIV-1 genome under control of the LTR and present the GFP gene replacing nef. The 8.4 cells display non-significant basal levels of GFP expression. Cells were incubated with the different treatments, and GFP expression was monitored in gated live cells at 72 h by standard flow cytometric techniques. Results are presented as fluorescence histograms. Each histogram reports the percentage of fluorescent cells beyond a threshold value established using non-infected Jurkat cells.

Figure 5:
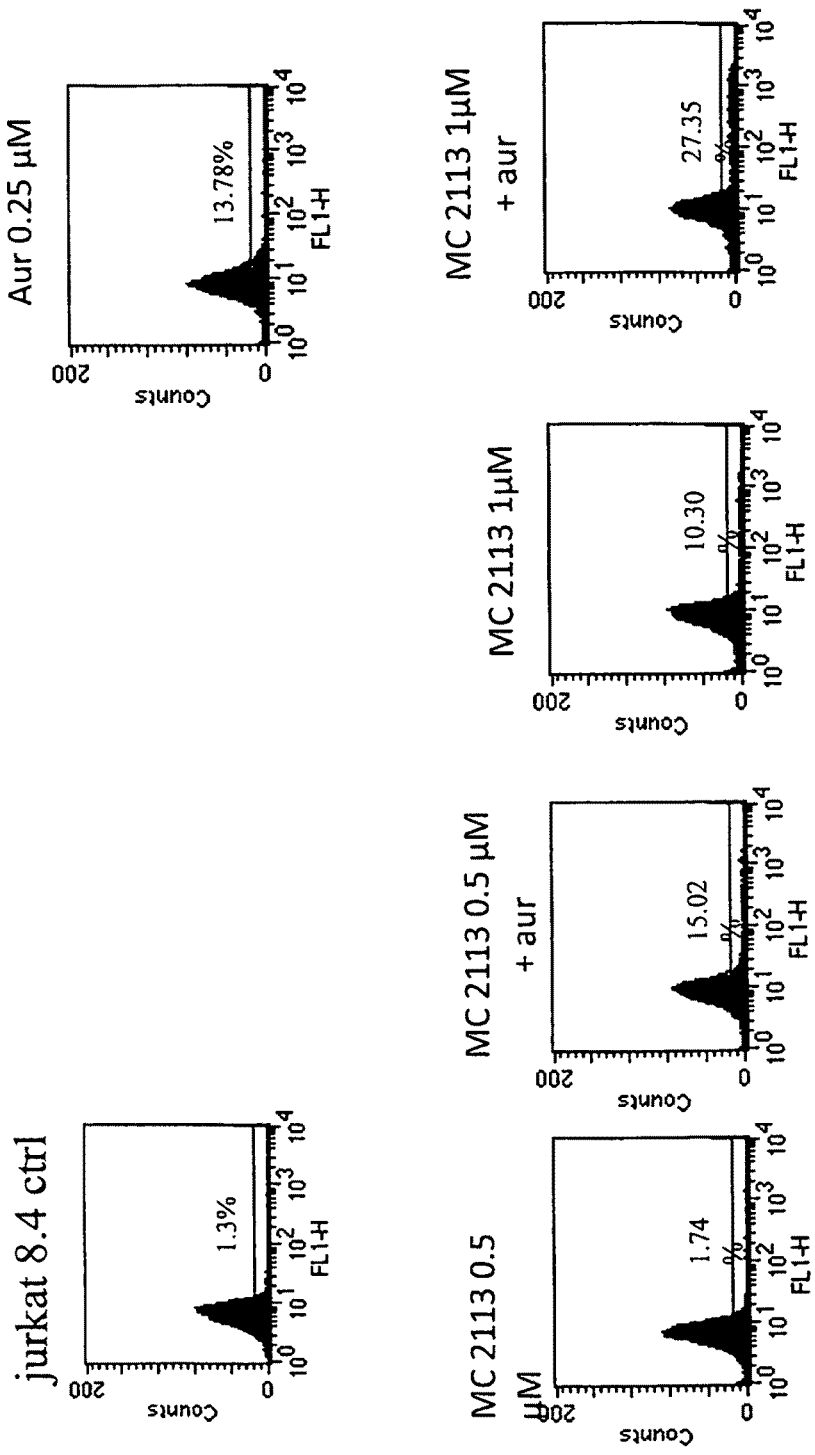

FIG. 5. Induction of LTR-controlled expression of green-fluorescent protein (GFP) by auranofin and a class I histone deacetylase inhibitor (MC2113). Quiescently infected Jurkat 8.4 cells were treated with a clinically relevant concentration of auranofin (0.25 microM) or 1 microM of MC2113, or both. Data are presented as in FIG. 4.

Figure 6:
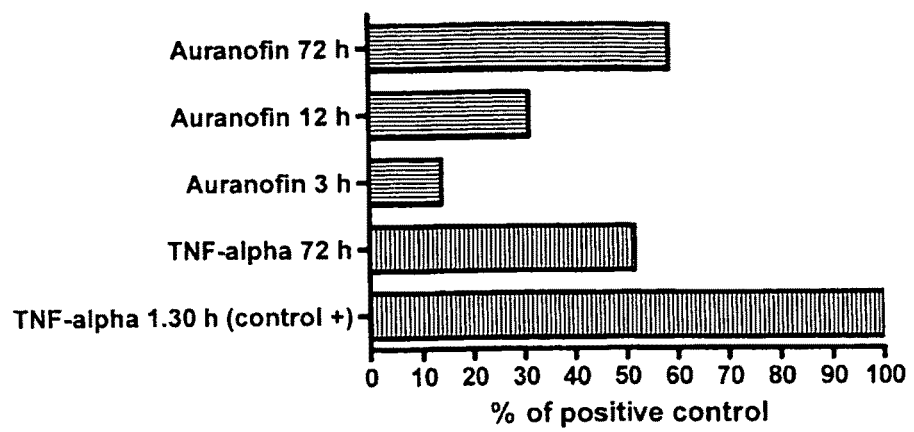

FIG. 6. Induction of NF-kappaB (p65/p50) nuclear transportation by auranofin at different incubation times. Quiescently infected Jurkat 8.4 cells were incubated with auranofin a clinically relevant concentration of auranofin (0.25 microM), and the presence of p65 in nuclear extracts was quantitated by a nuclear factor colorimetric assay. Results are presented as a percentage of the signal obtained in nuclear extracts from cells incubated with TNF-alpha for 1.5 h.

Figure 7:
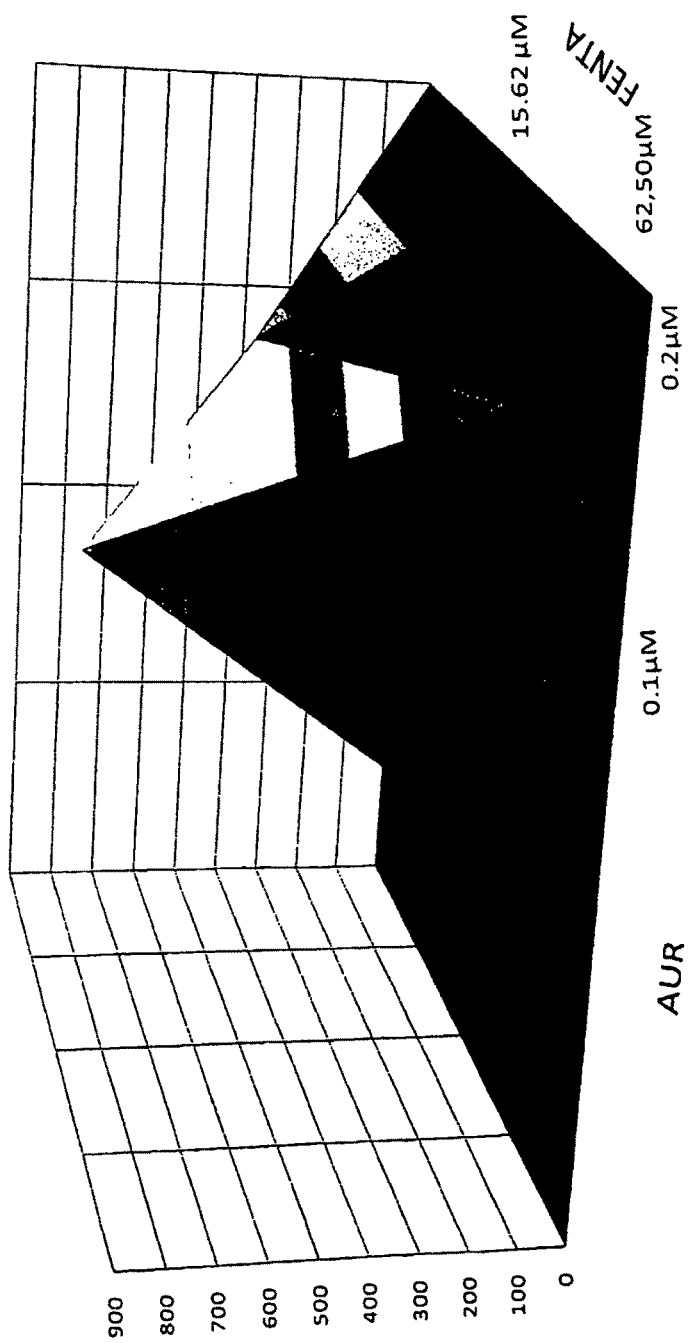

FIG. 7. Combined effects of auranofin and iron nitriloacetate (FeNTA) resulting in synergistic stimulation of HIV-1 replication in ACH-2 cells.

3D surface showing synergism between drugs. x,y axes: drug concentration; z axis: percentage of synergism between the two drugs. Percentage-of-synergism values represent the percent difference between the effects of the drug combination and the sum of the effects of auranofin and FeNTA administered separately at matched concentrations, calculated as follows:

$$PS = 100 \cdot [E_{drug\ A + drug\ B} - (E_{drug\ A} + E_{drug\ B})] / (E_{drug\ A} + E_{drug\ B})$$

where PS is the percentage of synergism and E is the effect of the drug concentration, expressed as the fold-increase in p24 production.

Figure 8:
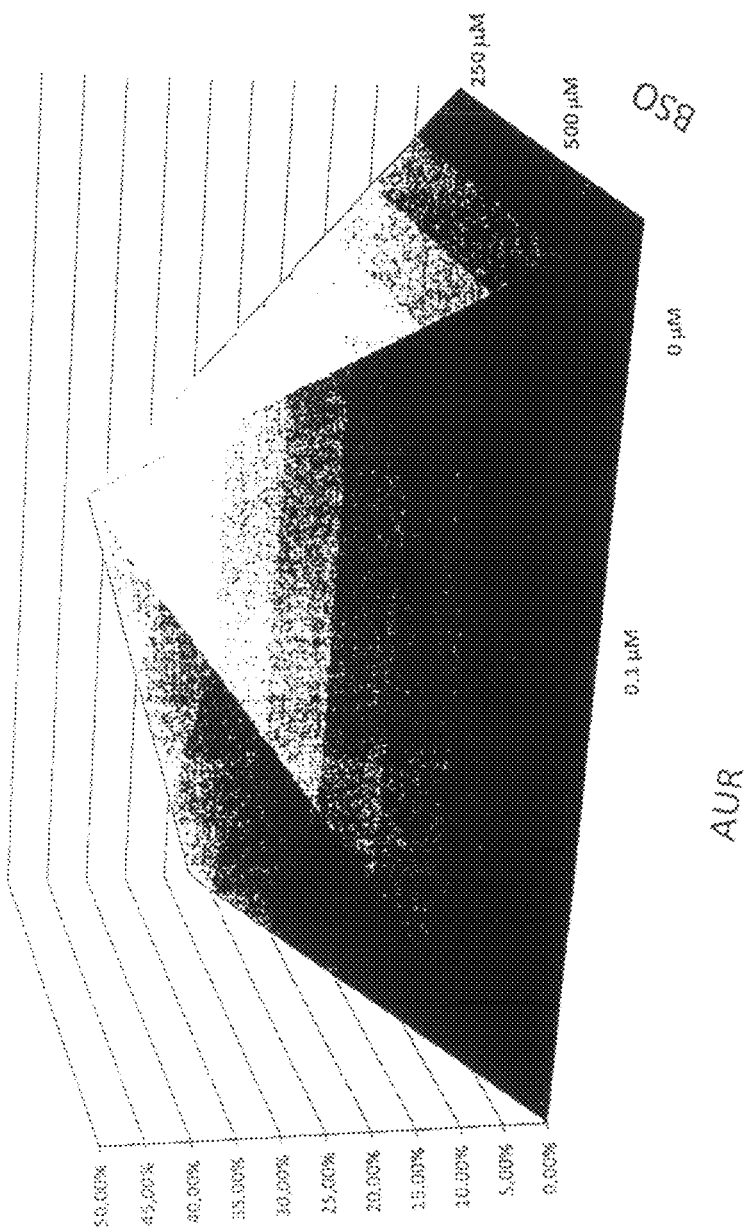

FIG. 8. Combined effects of auranofin and buthionine sulfoximine (BSO) resulting in synergistic stimulation of HIV-1 replication in ACH-2 cells. For figure interpretation the reader is addressed to caption of FIG. 7.

Figure 9:
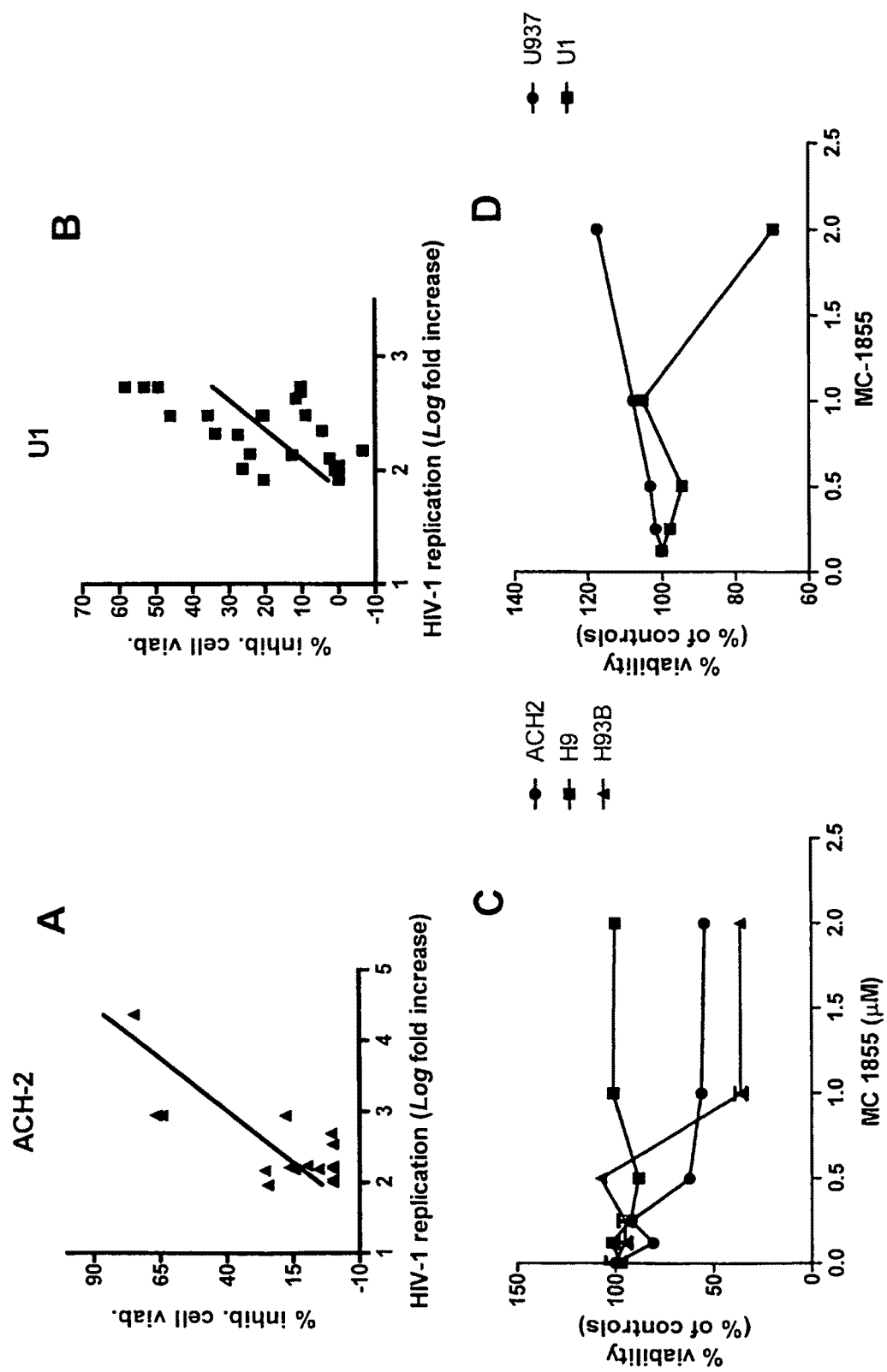

FIG. 9. Cell killing by histone deacetylase inhibitors (HDACi).

Panels A-B: Correlation between HIV-1 p 24 production in HDACi-treated latently infected ACH-2 (panel A) and U1 (panel B) cells and inhibition of infected cell viability. Cells were incubated with the test compounds (1 □M), and p24 production was measured by ELISA in cell culture supernatants. After collection of supernatants, cell viability was measured by the highly standardised methyl tetrazolium (MTT) method. x axis: fold-increase in HIV-1 p24; data are presented as a Log transform of the percentage of baseline levels in untreated cultures. y axis: percentage reduction in cell viability in comparison to untreated controls incubated under similar conditions. Panels C-D: Selective killing of HIV-1 infected lymphocytic (panel C) and monocytic (panel D) cell cultures by MC 1855. Non-infected H9, and U937, and HIV-1 infected H9$_{IIIB}$, ACH-2, and U1 cells were incubated with the test compounds for seven days, and cell viability was measured as described above. x axis: drug concentration. y axis: percentage reduction in cell viability in comparison to untreated controls.

Figure 10:
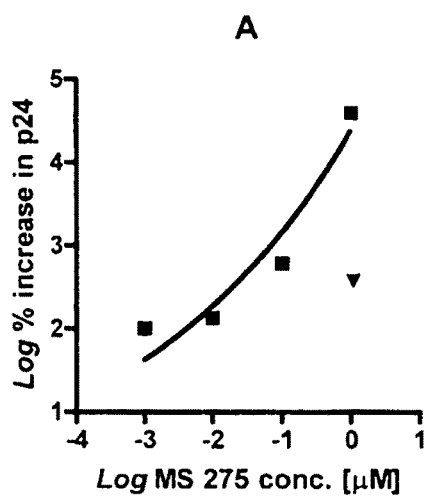

FIG. 10. Dose-dependent stimulation of HIV-1 replication by MS 275 in ACH-2 cells.

The graph shows the concentration-dependent stimulation of HIV-1 p24 production in ACH-2 cells at Day 3 of incubation with the drug. x axis: Drug concentration; y axis: fold-increase in HIV-1 p24 (Log transform of the percentage of baseline levels in untreated cultures). Appropriate transformations were adopted to normalise the data where necessary. The line or curve best fitting the data points is shown.

Figure 11:
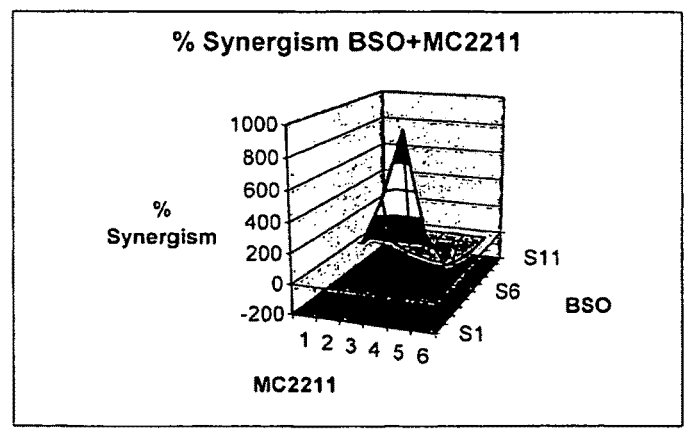
Figure 12:
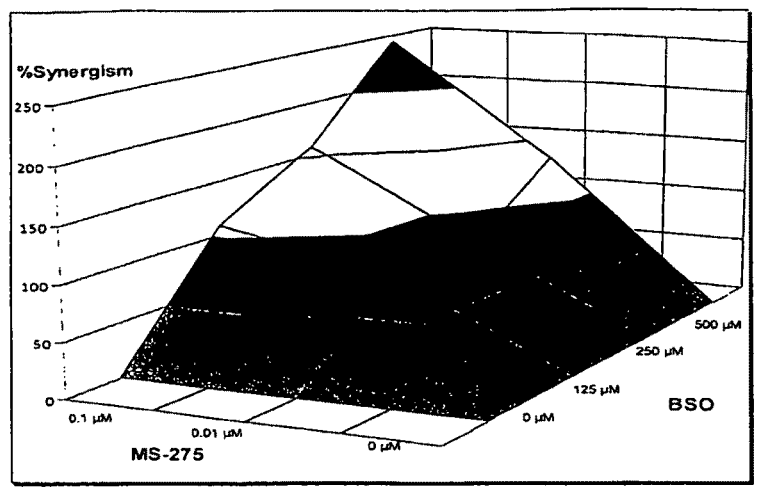

FIGS. 11 and 12. Synergism of histone deacetylase inhibitors (HDACi) with buthionine sulfoximine (BSO).

The three dimensional (3D) graph shows the 3D surface of synergism between each HDACi and BSO. x,y axes: drug concentration; z axis: percentage of synergism between the two drugs. Percentage-of-synergism values represent the percent difference between the effects of the drug combination and the sum of the effects of MS 275 and BSO administered separately at matched concentrations, calculated as follows:

$$PS = 100 \cdot [E_{drug\ A + drug\ B} - (E_{drug\ A} + E_{drug\ B})] / (E_{drug\ A} + E_{drug\ B})$$

where PS is the percentage of synergism and E is the effect of the drug concentration, expressed as the fold-increase in p24 production.

Figure 13:
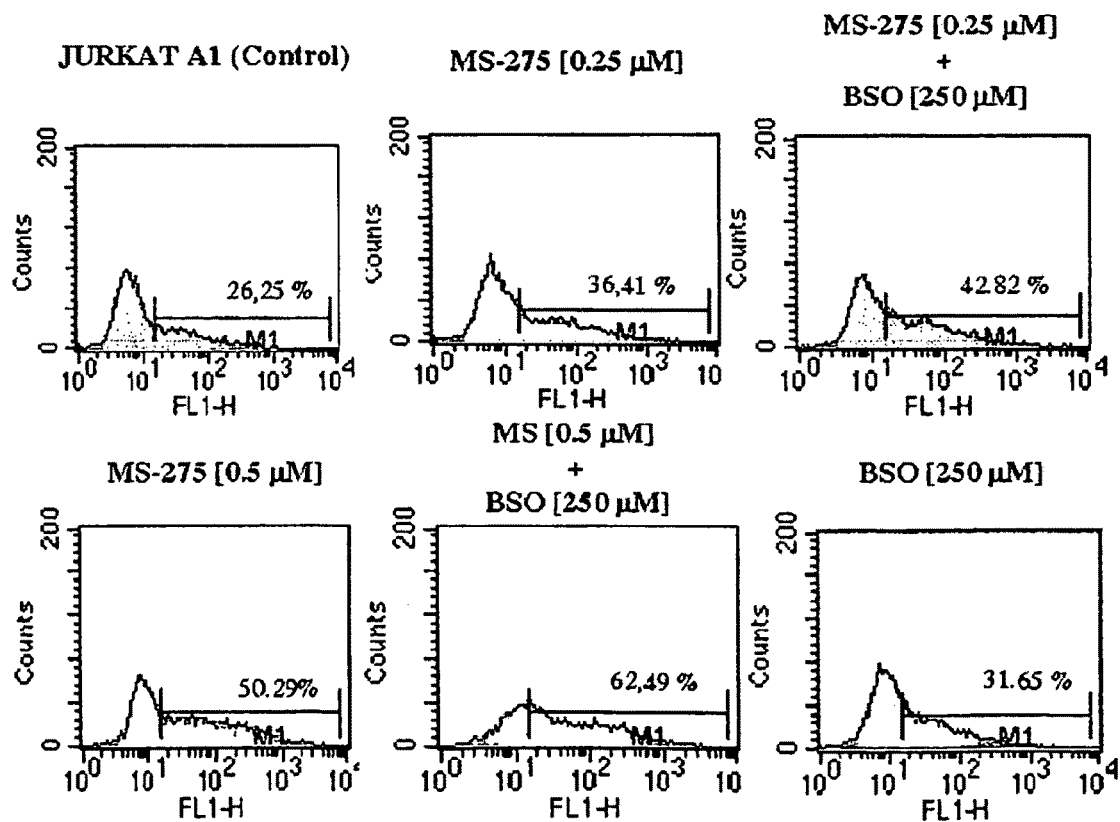

FIG. 13. Stimulation of HIV-1 LTR-controlled expression of green fluorescent protein (GFP) by MS-275 and buthionine sulfoximine (BSO), alone or in combination in a Jurkat cell clone (A1). The A1 cell clone, derived from T-lymphoid Jurkat cells, established by Jordan et al. as a model for latent HIV-1 infection. This clone has an integrated GFP/Tat construct under control of the HIV-1 LTR and displays a basal proportion of cells expressing GFP, which increase following stimuli activating the HIV-1 promoter. A1 cells were incubated for 72 h with the different treatments, and GFP expression was monitored by standard flow-cytometric techniques and assessed as the percentage of fluorescent cells (indicated for each histogram) beyond the threshold value established using control non-transfected Jurkat cells. One experiment out of three with similar results. The histograms derived from double-drug treatments were found to be significantly different (P<0.01) from those derived from treatments with the single drugs at matched concentrations (Kolmogorov-Smirnoff statistics).

Figure 14:
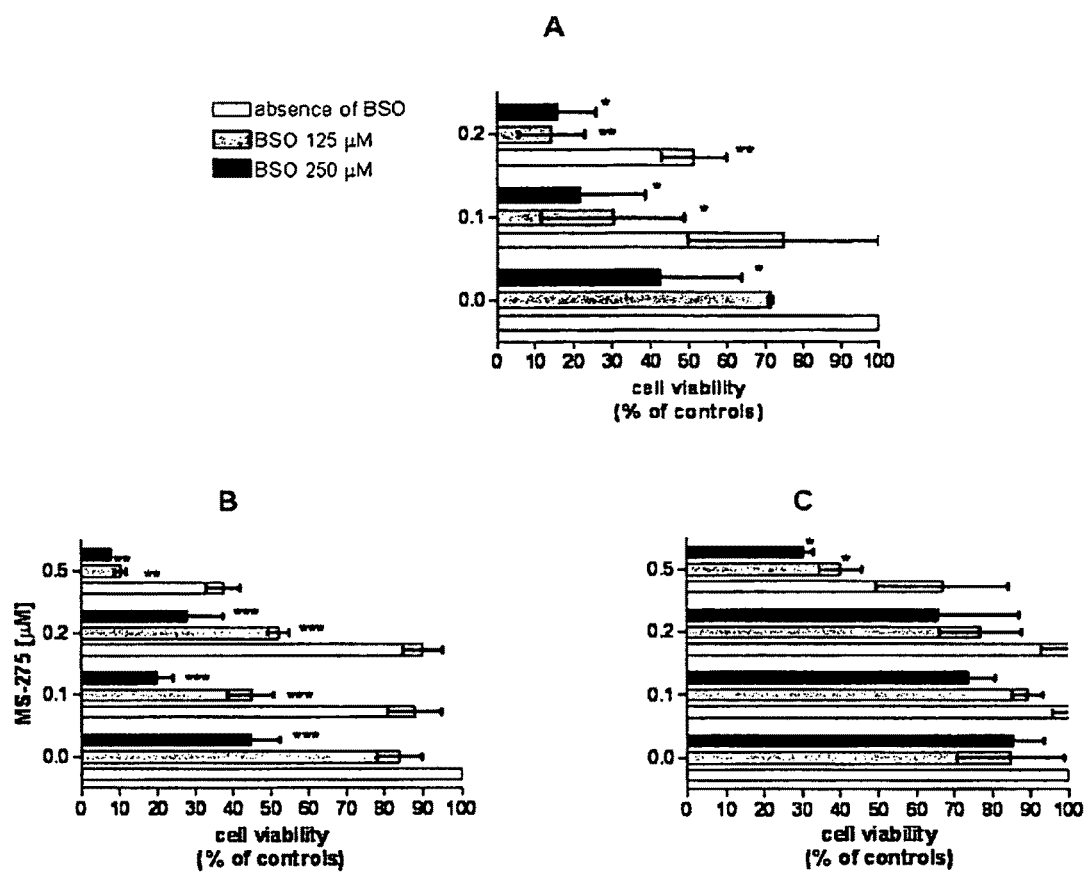

FIG. 14. Effects of HDAC inhibitor, MS-275 and buthionine sulfoximine (BSO), alone or in combination. Cell viability values are given at 72 h of incubation, as determined by the methyl tetrazolium (MTT) method: ACH-2 cells (A), Jurkat 6.3 cells (B), uninfected Jurkat cells (C). Results are presented as percentages of the absorbance ($\lambda$=550) in untreated controls subtracted of background (means±SEM; 3 experiments). Asterisks show the significant differences found between BSO treatments and matched treatments in the absence of BSO (*P<0.05; P<0.01; *P<0.001). Statistical significance was calculated using repeated-measures, two-way ANOVA and Bonferroni's post-test, following an appropriate transformation to restore normality, where necessary.

Figure 15:
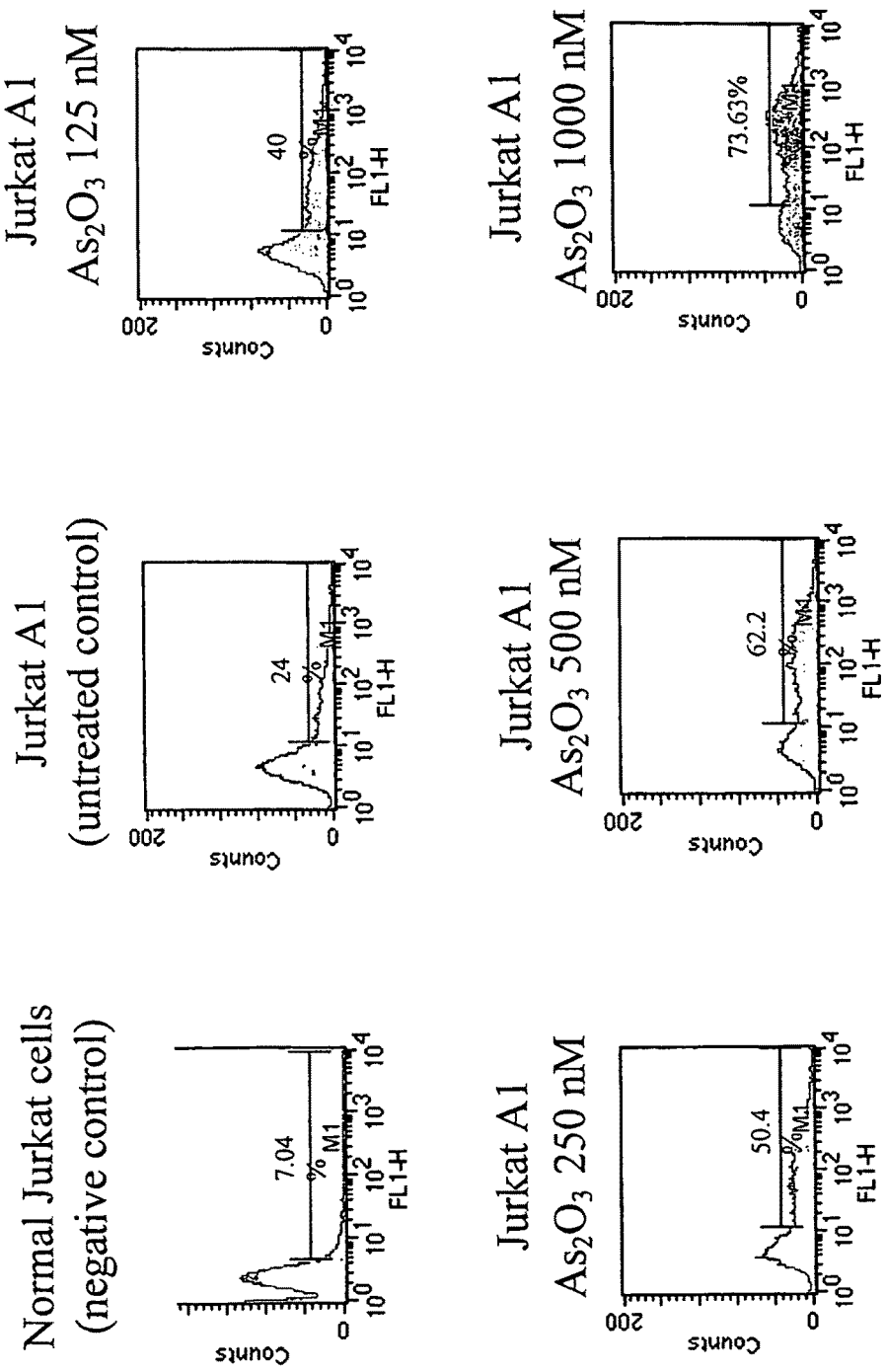

FIG. 15. Dose-dependent induction of LTR-controlled expression of green-fluorescent protein (GFP) by arsenic trioxide. In this experiment, we used the T-lymphoid Jurkat cell clone A1, which has an integrated GFP/Tat construct under control of the HIV-1 LTR. Cells were incubated with the different treatments, and GFP expression was monitored in gated live cells at 72 h by standard flow cytometric techniques. Results are presented as fluorescence histograms. Each histogram reports the percentage of fluorescent cells beyond a threshold value established using non-infected Jurkat cells.

DETAILED DESCRIPTION OF THE INVENTION

In an aspect, there is provided the use of a gold-containing compound in the treatment of a retroviral reservoir.

It is preferred that the gold-containing compound is capable of inducing retroviral replication in a recognised model of a reservoir of said retrovirus. In the case of HIV-1, this model may be selected from the U1 and ACH-2, for example. It is further preferred that compounds of the present invention have a minimum activity in the U1 assay described hereinunder in the accompanying Experimental section of around a 500% fold increase (%).

The preferred retrovirus is a simian or human lentivirus, such as HIV, for example. HIV-1 is the preferred target of the present invention.

Preferably, the gold-containing compound is auranofin (FIG. 1), which is characterized by its gold(I) central atom as well as a triethylphosphine and a carbohydrate ligand. Other related and preferred gold complexes include, for example, the chloro analogue: Et$_3$PAuCl and gold thiomalate. These may have multiple modes of action which are still being explored. Auranofin was recently shown to induce a shift towards the pro-oxidant side of the intracellular redox potential [Sannella et al., 2008]. The active species is likely the gold ion itself and the ligands are more relevant for the biodistribution and kinetic properties of the agents. Ideal candidates for HIV-1 eradicating strategies should not induce immune activation (detrimental for HIV-1-infected individuals [Savarino et al., 2000]). It is, therefore, advantageous that organic gold salts are endowed with anti-inflammatory properties.

The gold (I) or (II) ion is, therefore, bioavailable. It will be appreciated that the gold-containing compound can also be referred to as a complex. The gold-containing compound may comprise gold in its (I) or (II) oxidation state, with (I) being particularly preferred. The gold-containing compounds of the invention are ionic chemical compounds of gold or organogold compounds.

Preferably, the gold-containing compound can be used either alone or in combination with at least one of an HDACi, BSO and/or iron nitoloacetate. Combinations with BSO are preferred and combinations with at least one HDACi are particularly preferred.

The invention also provides the use of an oxidative stress inducer, which is a non-iron metallodrug epigeneitic modulator, in combination with at least one HDACi in the treatment of a retroviral reservoir. The oxidative stress inducer is most preferably a gold- or arsenic-containing compound, such as auranofin or arsenic trioxide, or a glutathione synthesis inhibitor, such as BSO. Iron Nitroloactate is also envisaged in combination with an HDACi.

To the extent that HDACi's may be considered as oxidative stress inducers, the oxidative stress inducer mentioned above is a non-HDACi oxidative stress inducer. In other words, the invention may provide the use at least one HDAC in combination with at least one other (non-HDACi) oxidative stress inducer in the treatment of a retroviral reservoir. Said other (non-HDACi) oxidative stress inducer may be auranofin or BSO, iron nitriloacetate or ferrous sulphate, for instance.

Methods of treatment, corresponding to the present uses are also envisaged.

It will be appreciated that reference herein to iron nitriloacetate applies to range of iron-containing compounds having a similar activity in vitro or in vivo. Another suitable example is ferrous sulphate. The terms are thus interchangeable unless otherwise apparent.

Oxidative stress was shown to be linked to HIV-1 replication by binary interactions, with HIV-1 replication sparking oxidative stress, and oxidative stress activating HIV-1 from quiescence [Israël and Gougerot-Pocidalo, 1997]. The mechanisms behind the oxidative stress-induced HIV-1 activation from quiescence are numerous and are still poorly explored. Oxidative stress was shown to drive the balance between the activities of histone deacetylases (HDACs) and histone acetyl transferases (HATs) towards an increased HAT activity [Rahman et al., 2004]. This favors DNA unwinding and transcription of several genes, including the HIV-1 provirus. Nevertheless, the use of oxidative stress inducers in combination with HDACi's has not been contemplated.

Auranofin may not necessarily induce HIV-1 reactivation through oxidative stress, it may act via an alternative mechanism. We have shown that auranofin induces HIV-1 activation from quiescence, likely by a novel mechanism. Evidence that this drug activates HIV-1 from quiescence is derived from its reproducible effects in four different cell lines in which LTR-driven gene expression is inducible. The view that auranofin activates HIV-1 gene expression by a novel mechanism is suggested by its effects in combination with drugs known to activate HIV-1 gene transcription by different and well characterized mechanisms, and is supported by the extant literature on its intracellular targets [Rigobello et al., 2002; Rigobello et al., 2005; Omata et al., 2006; Talbot et al., 2008].

Auranofin was shown to be an inhibitor of TrxRs, which are selenoproteins involved in maintenance of the intracellular redox homeostasis [Rigobello et al., 2002; Rigobello et al., 2005; Omata et al., 2006]. Auranofin was also shown to inhibit the synthesis of TrxRs [Talbot et al., 2008]. TrxRs are found in two main isoforms, one cytosolic (TrxR1) and one mitochondrial (TrxR2) [Lu and Holmgren, 2009]. TrxRs have several substrates, the principal of which is thioredoxin (Trx1 is the cellular isoform; Trx2 is the mitochondrial isoform). TrxRs maintain Trx in a reduced state which in turn reduces several intracellular proteins. Apart from Trx, TrxRs also reduce other targets including HIV-1 Tat, which is inactivated by action of TrxR (Kalantari et al., 2008).

In light of this evidence, one could surmise that the effects of auranofin on HIV-1 reactivation could be mediated by Tat. Auranofin, however, carried out HIV-1 inducing effects in cell lines such as ACH-2 and U1, which have a defective Tat/TAR axis, thus suggesting that other targets are involved in the HIV-1 inducing effects of auranofin. Auranofin, in fact, was shown to act on multiple intracellular targets. Apart from its effects on selenoproteins, this drug was found to inhibit some kinases such as protein kinase C [Daniel et al., 1995], cathepsins [Chircorian and Barrios, 2004].

In our study, auranofin potently enhanced the HIV-1 activating effects of FeNTA, which generates reactive oxygen species (ROIs) through the Fenton reaction. Moreover, the effects of auranofin were enhanced by BSO, a compound that induces glutathione depletion and therefore decreases the ability of cells to counteract oxidative stress. If, as other authors (Sannella et al., 2009) report, auranofin induces pro-oxidant effects, its mechanism may be distinct from those of other pro-oxidant molecules such as FeNTA and BSO. The HIV-1 activating effect of auranofin alone is herein supported by its NF-kappaB activating effects. Oxidative stress was shown to induce NF-kappaB (p65/p50) nuclear translocation [Rahman et al., 2004]. This nuclear factor binds to specific sites on the HIV-1 LTR and promotes transcription of the proviral genome [Williams et al., 2007].

In this regard, we found in the present study that auranofin induces NF-kappaB nuclear translocation and DNA binding under conditions similar to those at which it induces HIV-1 replication. This was a really surprising finding, in light of previous reports [Jeon et al., 2000; Traber et al., 1999]. Apparent discrepancies between our results and those of previous studies showing an inhibitory effect of auranofin and other gold-containing compounds on NF-kappaB activation [Jeon et al., 2000; Traber et al., 1999], can be reconciled by considering the different drug concentrations adopted. The auranofin concentrations adopted in the previous studies to show NF-kappaB inhibition were approx. two orders of magnitude superior to those adopted in the present study. Such drug concentrations, which are superior to those clinically achievable in the treatment of rheumatoid arthritis, were toxic to our cell lines (data not shown). Instead, we have shown that auranofin can have the opposite effect to HIV silencing, namely activation. This is particularly the case at suitable concentrations, as will be easily determined by the skilled person. By way of guidance, however, it is preferred to use a 0.125-0.5 microM range of concentrations, approximating the mean plasma levels observed during treatment of rheumatoid arthritis [Benn et al., 1991, herein incorporated by reference]. Other preferred ranges include 0.1-0.6, 0.125-0.3, 0.2-0.6, 0.2-0.7, 0.125-0.2 and 0.125-0.175 microM.

The skilled person will appreciate that these can be upscaled to human dosages, but any one of the following ranges is preferred: 0.025-0.2 mg/kg/day, 0.02-0.3 mg/kg/day, 0.01-0.3 mg/kg/day, 0.005-0.3 mg/kg/day, 0.03-0.2 mg/kg/day, 0.03-0.4 mg/kg/day, 0.025-0.4 mg/kg/day and 0.02-0.5 mg/kg/day. A dosage range of 0.025-02 mg/kg/day is particularly preferred.

The auranofin-induced NF-kappaB nuclear translocation, though further supporting the view that auranofin activates HIV-1 from quiescence by induction of an oxidative stress, cannot be taken as an evidence pointing to NF-kappaB as the main effector for the effects of auranofin on HIV-1 replication. Several other transcriptional factors potentially active on the HIV-1 LTR are activated by oxidative stress [Wu et al., 2004]. Moreover, oxidative stress switches the balance between HDAC and HAT activities towards increased activity of HATs. In this regard, we found synergistic effect of auranofin and HDACIs.

Although gold ions (I and II) alone are poor Fenton catalysts, organic complexes of gold may enhance the Fenton reaction catalyzed by $Fe^{2+}$ by acting as superoxide dismutase (SOD) mimics [Huang et al., 2005]. SOD mimics, by catalyzing the superoxide/peroxide conversion, may replenish the intracellular hydrogen peroxide pools consumed by the Fenton catalyst, thus furnishing new substrate to the Fenton reaction. SOD mimicry and TrxR inhibition that are not necessarily mutually exclusive and may have a common background. Thus, it is possible to hypothesize that both mechanisms cooperate to activate HIV-1 from quiescence. Finally, we cannot exclude that other, as yet unexplored mechanisms may underlie the HIV-1 activating effect of auranofin.

The results of the present study suggest a new application for existing drugs in induction of HIV-1 activation from quiescence. It also suggests novel strategies based on two-drug combinations activating HIV-1 at non-toxic drug concentrations. Auranofin is a drug successfully used for treatment of rheumatoid arthritis and leukemia was found in the present study to induce HIV-1 activation from quiescence at clinically achievable concentrations, which have a toxicity profile that is well-characterized and shown not to endanger human health. Moreover, we show that effective auranofin concentrations can be further decreased by concomitant use of other HIV-1 activating agents such as HDACIs, acting by different mechanisms.

Our results showed that auranofin induced a time- and dose-dependent HIV-1 reactivation (P=0.0295, t-test for regression; FIG. 5B) in the 0.125-0.5 microM range of concentrations, approximating the mean plasma levels observed during treatment of rheumatoid arthritis [Benn et al., 1991]. In line with its capacity to induce HIV-1 activation, auranofin induced nuclear translocation of NF-kappaB, an important transcription factor for HIV-1. The effects of auranofin on HIV-1 activation from quiescence were additive or synergistic with those of other compounds enhancing HIV-1 replication. These included histone deacetylase inhibitors (HDACIs), which favor HIV-1 transcription by epigenetic regulation of DNA unwinding, iron nitriloacetate, which promotes HIV-1 transcription by intracellular generation of reactive oxygen species (ROIs), and buthionine sulfoximine, a glutathione synthesis inhibitor that impairs the cell's capacity to counteract oxidative stress. These combined effects allow use of both auranofin and each of the aforementioned drugs at concentrations that are non-toxic for uninfected cells.

Finding possible cures for HIV-1/AIDS, capable of eradicating the virus from the body, is a major scientific challenge for the $21^{st}$ century. One further avenue of investigation is aimed at investigating potential drugs and drug combinations useful for the elimination of latent HIV-1 reservoirs that persist despite antiretroviral therapy (ART). This involves overcoming the latent barrier by inducing the replication of HIV in latently infected T cells while preventing the spread of the newly produced virions to uninfected cells by providing ART simultaneously. Histone deacetylase inhibitors (HDACi's) have been postulated to be potentially useful tools in HIV-1 eradication strategies [Demonté et al., 2004], and valproic acid (VA), a relatively weak HDACi, was shown to promote HIV-1 escape from latency in vitro and to reduce the numbers of latently infected memory $CD4^+$ cells in vivo in combination with antiretroviral therapy [Lehrman et al., 2005; Smith, 2005]. Such strategies have been dubbed "shock and kill"

[Hamer, 2004]. The low potency of VA ($EC_{50}$ in the millimolar range) is likely to have contributed to its failure to induce HIV-1 eradication.

Novel and more potent HDACi have been developed for inducing differentiation in tumours [Mottet and Castronovo, 2008]. Many of the new agents, however, are non-specific inhibitors for all types of HDAC, which variously play important roles in the cell cycle [Dokmanovic et al., 2007]. Class I HDACs comprise HDAC1-3 and 8, are predominantly nuclear enzymes and are ubiquitously expressed [Annemieke et al., 2003]. Class II HDACs comprise HDAC4-7,9 and 10 and shuttle between the nucleus and the cytoplasm [Annemieke et al., 2003]. HDAC1 likely maintains HIV-1 latency by acting in a multi-molecular complex with c-Myc and LTRs [Williams et al., 2006; Jiang et al., 2007].

Other strategies have been explored for inducing HIV-1 escape from latency, including use of the natural substance prostratin (whose mechanisms are, so far, largely unexplored) and diacyl glycerol lactones that interfere with T-cell activation [Hezareth, 2005; Hamer; 2004].

Oxidative stress is another potent means promoting HIV-1 replication [Hulgan et al., 2003; Savarino et al.; 1999; Garaci et al., 1997; Palamara et al., 1996]. Reactive oxygen intermediates promote activation and nuclear translocation of nuclear factor-kappaB (NF-kappaB) [Bowie and O'Neill, 2000], a transcription factor enhancing HIV-1 transcription and replication, which can be inhibited by high concentrations of glutathione and other antioxidants [Palamara et al., 1996]. Small molecule redox state modulators have, so far, been poorly explored for their HIV-1 eradication potential.

We have now, surprisingly, found that two types of HDACi inhibitor, the benzamides and the hydroxamates, show remarkable activity in activating reservoirs of latent retrovirus preferably in combination with the glutathione-synthesis inhibitor, buthionine sulfoximine (BSO). In combination with known antiretroviral therapy or treatment (ART), this may then be used in therapy to reduce or eliminate retrovirus infection.

Specifically, benzamide and hydroxamate inhibitors of histone deacetylases have been found to stimulate the reproduction of retroviruses from latent reservoirs thereof, and this may be used to reduce or eliminate these reservoirs in combination with conventional antiretroviral therapy. Further, buthionine sulfoximine (BSO) has been found to substantially potentiate the anti-retroviral activity of the benzamide HDACi's. Analogues of BSO are also preferred.

In an aspect of the invention, there is provided the use of a histone deacetylase inhibitor (HDACi) of either the benzamide or the hydroxamate variety in the treatment of a retroviral reservoir. It is particularly preferred that the HDACi is used in combination with BSO.

It is preferred that the inhibitor is capable of inducing retroviral replication in a recognised model of a reservoir of said retrovirus. In the case of HIV-1, this model may be selected from the U1 and ACH-2, for example. It is further preferred that compounds of the present invention have a minimum activity in the U1 assay described hereinunder in the accompanying Experimental section of 800 fold increase (%).

As with gold-containing compounds, the preferred retrovirus is a simian or human lentivirus, such as HIV-1, for example, and HIV-1 is the preferred target.

Thus, HDACi's may be used in a number of aspects of the invention, for instance with oxidative stress inducers or. The oxidative stress inducer may include gold-containing compounds, such as auranofin, arsenic compounds, such as arsenic trioxide, or glutathione synthesis inhibitors, such as BSO. Preferred HDACi's for use in all aspects of the invention as described below.

So-called "classical" HDIs act on Class I and Class II Histone Deacetylases. The classical HDACi bind to the zinc containing catalytic domain of the HDACs. These classical HDIs fall into several groupings. These include hyroxamic acids, such as Trichostatin A; cyclic tetrapeptides (such as trapoxin B), and the depsipeptides; benzamides; electrophilic ketones; and aliphatic acid compounds such as phenylbutyrate and valproic acid. So-called "Second generation" HDIs include SAHA/Vorinostat, Belinostat/PXD101, MS275, LAQ824/LBH589, CI994, and MGCD0103. The sirtuin Class III HDACs are NAD+ dependent and are therefore inhibited by nicotinamide, as well derivatives of NAD, dihydrocoumarin, naphthopyranone, and 2-hydroxynaphaldehydes. Suberoylanilide Hydroxamic Acid (SAHA) particularly preferred, especially in combination with gold-containing compounds such as auranofin.

Particularly preferred HDACi's are benzamide HDACi's. These may have the formula:

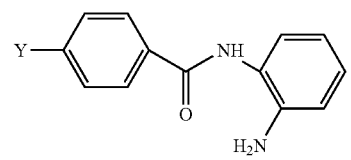

in which Y comprises one or two six-membered rings, each being unsaturated or partially unsaturated and heterocyclic or homocyclic, with two to eight linking atoms, and wherein either the linking atoms or a ring comprises an amino group and a carbonyl group.

More preferred benzamides are the close analogues of the compounds identified as MC 2211, MC2113 and MS 275 below are particularly preferred, and MS 2113 is most preferred.

MC 2211 is:

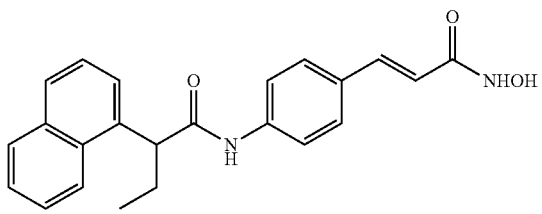

MC2113 is:

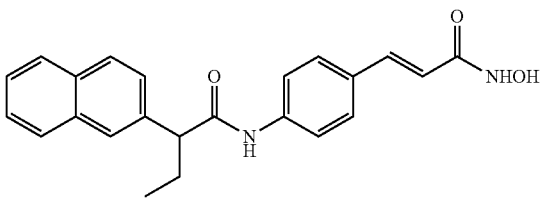

MS 275, or N-(2-aminophenyl)-4-[N-(pyridin-3-yl-methoxycarbonyl)aminomethyl]-benzamide), is disclosed in EP1626719, and has the structure:

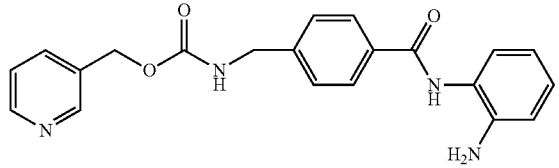 [SMILES: Nc1ccccc1NC(=O)c1ccc(CNC(=O)OCc2cccnc2)cc1]

Preferred hydroxamate HDACi's have the formula:

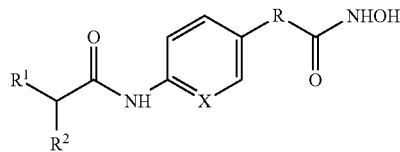

wherein R is a direct bond or an ethylene or ethenylene group, X is =CH— or =N—, $R^1$ is aryl or heteroaryl, and is mono- or bi-cyclic, and $R^2$ is straight or branched chain alkyl, optionally substituted by a mono- or bi-cyclic aryl or heteroaryl group. Preferably, $R^2$ is unsubstituted alkyl, preferably methyl, ethyl, or isopropyl. $R^1$ is preferably phenyl or naphthyl. R is preferably ethenylene. X is preferably =CH—. Preferred HDACi's are the Class 1 HDACi's.

Also preferred are hydroxamate HDACi's such as Suberoylanilide Hydroxamic Acid (SAHA). This is a hydroxamic acid-containing hybrid polar molecule and specifically binds to and inhibits the activity of histone deacetylase. SAHA is known in the art to exhibit an antitumor effect by increasing expression of genes regulating tumor survival and to SAHA reduce the production of proinflammatory cytokines in vivo and in vitro (Mascagni et al, "The antitumor histone deacetylase inhibitor suberoylanilide hydroxamic acid exhibits anti-inflammatory properties via suppression of cytokines" PNAS Mar. 5, 2002 vol. 99 no. 5 2995-3000).

The use of a histone deacetylase inhibitor (HDACi) in the treatment of a retroviral reservoir is also envisaged. The inhibitor may be selected from the HDACi's discussed herein and preferably:

a) a benzamide HDAC inhibitor having the formula:

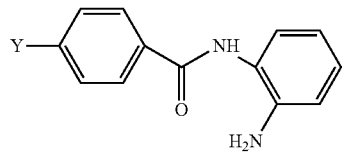

in which Y comprises one or two six-membered rings, each being unsaturated or partially unsaturated and heterocyclic or homocyclic, with two to eight linking atoms, and wherein either the linking atoms or a ring comprises an amino group and a carbonyl group; or b) a hydroxamate HDAC inhibitor having the formula:

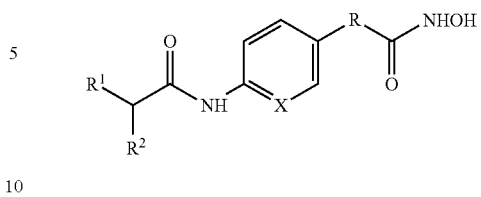

wherein R is a direct bond or an ethylene or ethenylene group, X is =CH— or =N—, $R^1$ is aryl or heteroaryl, and is mono- or bi-cyclic, and $R^2$ is straight or branched chain alkyl, optionally substituted by a mono- or bi-cyclic aryl or heteroaryl group. Preferably, the HDACi is a class I HDACi.

Preferably, the inhibitor is capable of inducing retroviral replication in a recognised model of a reservoir of said retrovirus. The retrovirus may be an HIV virus, preferably HIV-1 and the model may be selected from the U1 and ACH-2 cellular models.

Preferably, the benzamide is a close analogue of one of the compounds identified as MC 2211 and MS 275 herein. The inhibitor may be a compound having the formula:

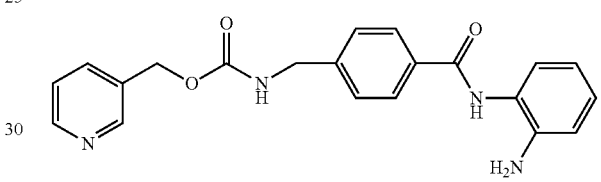

Preferably, $R^2$ is an unsubstituted alkyl, preferably methyl, ethyl, or isopropyl. Preferably, $R^1$ is phenyl or naphthyl. R is preferably ethenylene. X is preferably =CH—.

It is preferred that the inhibitor is a Class 1 inhibitor and is not non-specific. Preferably, the treatment includes, in addition, anti-retroviral therapy.

The use of a histone deacetylase inhibitor (HDACI), particularly of the benzamide variety, in combination with a glutathione synthesis inhibitor, such as BSO (buthionine sulfoximine), in the treatment of a retroviral reservoir is also provided. Preferably, the inhibitor is N-(2-aminophenyl)-4-[N-(pyridin-3-ylmethoxycarbonyl)aminomethyl]-benzamide). It is preferred that the BSO and benzamide HDACi are administered together.

The accompanying Example 2 provides suitable techniques to establish which Class of HDAC compounds of the invention inhibit. It is particularly preferred that the HDACi's of the invention are not non-specific HDACi's.

The HDACi's of the present invention may be used in the treatment of patients suspected of having latent reservoirs of retroviruses. Such retroviruses will be referred to herein as HIV-1, although it will be appreciated that this is for convenience, and that all such references include references to other retroviruses, unless otherwise apparent from the context.

The treatment is preferably intended to eliminate any latent reservoir of retrovirus. However, it will be appreciated that such treatments may also be used, less preferably, to control latent retrovirus. This may be advantageous where an individual is particularly susceptible to repeat infections from the reservoirs, for example.

A latent reservoir is a cell or cells containing the retrovirus either in quiescence, or replicating at low rates, such as less than 5% of the normal rate, such that the cell can act to protect the virus for a period of time, and often only releases viable virions weeks or months after normal antiretroviral treatment has stopped, thereby requiring continued treatment of the individual, in case infection recurs through such a reservoir.

The 'normal' antiretroviral treatment referred to above, and which is administered to HIV-1-infected individuals, generally consists of a combination of at least three different drugs belonging to different classes, and are normally selected from the nucleosidic/nucleotidic reverse transcriptase inhibitors (NRTI's), the non-nucleosidic reverse transcriptase inhibitors (NNRTI's), and the protease inhibitors (PIs). A fusion inhibitor may also form a part of the treatment. Recently, a further drug class, the integrase inhibitors, has been added to the arsenal of antiretroviral drugs. Antiretroviral drug combinations, in general, show the capacity to block ongoing viral replication, but have no potential for eradicating the virus from the body.

For the elimination of retroviral reservoirs, current strategies postulate the use of HDACi's, especially the Class 1 HDACi's, together with conventional anti-retroviral therapy, as well known in the art, and as described above, for example [Savarino et al. 2009].

WO2007/121429 (Gladstone Institute), WO 03/053468 (Univ Libre Bruxelles) relate to uses of HDACi's. various HDACi structures are disclosed in WO 2004/069823 (Methylgene, Inc) and WO 2004/103369 (Schering A G). Munier S et al (Retrovirology, 23, Nov. 2005, 2:73) describes characterisation of two candidate genes, NCoA3 and IRF8, which may be involved in the control of HIV-1 latency. Garaci at al (Journal of Leukocyte Biology, July 1997, Vol 62, No. 1, pp 54-59) describes certain uses of BSO.

The HDACi may be administered direct to the patient in any suitable, pharmaceutically acceptable vehicle, and by any suitable route, as may be determined by a skilled person or physician. The HDACi may be administered as an injection or by transdermal patch, for example, and may be in free solution, or bound to a carrier. Other formulations, such as tablets, suppositories, creams and sprays will generally be less useful, although they may be used if deemed appropriate.

Suitable vehicles may include targeted liposomes, bearing suitable antibodies, but infected latent cells are largely associated with the circulation, so administration by intravenous injection is a particularly preferred route.

The present invention also provides the novel compounds of Table 1 and, independently, methods for making such, as illustrated in the accompanying Experimental section.

The present invention further provides pharmaceutically acceptable formulations of the novel compounds of the invention.

The present invention further provides a method for the selective elimination of latently infected cells, wherein the cells are latently infected by a lentivirus, especially HIV-1, said treatment comprising contacting said cells with an HDACi of the invention in combination with antiretroviral therapy.

What is particularly surprising is that the preferred benzamide HDACi's of the present invention have been found to be potentiated by buthionine sulfoximine (BSO) at levels of up to 800%. This particularly surprising as BSO has no appreciable anti-HIV-1 activity, but is capable of synergistic action with MS 275, for example, to very substantially increase its ability to kill cells having a latent HIV-1 infection.

This potentiation has the added advantage of reducing the amount of HDACi and BSO needed for treatment of the patient. For example, both MS 275 and BSO have been already tested for safety in humans, and amounts of MS 275 as used for cancer treatment are generally greater than are necessary for the treatment provided by the present invention.

The preferred dosage range for M δ 275 is in a range of about 0.05-0.1 mg/kg once weekly, or as prescribed by the physician. BSO may be administered contemporaneously with MS 275, at a preferred dosage of 0.1-0.3 mg/kg, and subsequent doses, preferably three to five in number, may be administered once or twice a day, preferably every 12 h.

Thus, the present invention further provides the use of a histone deacetylase inhibitor, preferably of the benzamide variety, in combination with buthionine sulfoximine, in the treatment of a retroviral reservoir.

The above-described method for selective elimination of latently infected cells further preferably comprises contacting said cells with BSO in combination with said HDACi, preferably in timings as described herein.

Although the BSO and HDACi work synergistically, neither is toxic, and the two may be administered together or separately, provided that both are present in vivo, particularly preferably in synergistic amounts. BSO may be formulated with the benzamide, or may be administered separately if there are any problems formulating the two active ingredients, or if the stability conditions for one are not compatible with the other, for instance.

As noted above, in general, it has been found that Class I selective HDACi show lower toxicity than non-selective compounds, and induce selective killing of HIV-1 infected U1, ACH-2, and H9 IIIB cells, compared with their uninfected counterparts ($P<0.01$, t-test for slope).

We compared the toxicity of the BSO+HDACi combination in uninfected and latently infected cell lines. Results showed that, using BSO in combination with HDAC is, there was marked cytotoxicity at 72 h of incubation in latently infected but not in uninfected cell cultures (FIG. 14). Apart from amplifying the effect of histone deacetylase inhibitors, the results of the present study allow us to hypothesise that our strategy using pro-oxidant agents such as BSO in combination with HDAC is able to induce selective killing of the latently infected cells.

This strategy can be considered to be one of the long-sought "shock and kill" strategies. These strategies consist of inducing, through drugs, HIV-1 activation from quiescence (i.e. the "shock" phase), in the presence of ART (to block viral spread), followed by the elimination of infected cells (i.e. the "kill" phase), through either natural means (e.g. immune response, viral cytopathogenicity) or artificial means (e.g. drugs, monoclonal antibodies, etc.) [Hamer D H, 2004]. Indeed, our strategy is based on an HDACi, which activates HIV-1 replication in latently infected cells (i.e. the "shock" phase), in combination with a pro-oxidant agent such as BSO, which amplifies the HDCAi response and causes cellular damage due to the HIV-1 induced decay in the intracellular levels of reduced glutatione (i.e. the "kill" phase). The search of a drug combination capable of exerting such effects has, so far, been a "Holy Grail" in AIDS research.

We have shown herein that gold-containing compounds are useful in the treatments of the present invention. Surprisingly, we have also found that arsenic-containing compounds are similarly useful.

Thus, the invention also provides for the use of an arsenic-containing compound in the treatment of a retroviral reservoir. Preferably, the compound is capable of inducing retroviral replication in a recognised model of a reservoir of said retrovirus. The retrovirus may be HIV-1 and the model may be selected from the U1 and ACH-2 cellular models. The retrovirus is preferably an HIV virus. Preferably, the arsenic-containing compound is an arsenic oxide, such as $As_4O_6$, although arsenic trioxide ($As_2O_3$) is particularly preferred.

Preferably, the use may further comprise the use of at least one further oxidative stress inducer, such as a non-iron metallodrug epigeneitic modulator, for instance gold-containing compounds, such as auranofin; a histone deacetylase inhibitor (HDACi); a pro-oxidant molecule, for instance a glutathione synthesis inhibitor such as BSO; and/or iron nitriloacetate or ferrous sulphate. The HDACi is preferably any of those defined above, and particularly from class I HDACi's.

The HDACi's may be:
a benzamide HDACi having the formula:

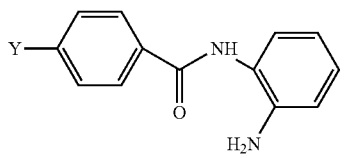

in which Y comprises one or two six-membered rings, each being unsaturated or partially unsaturated and heterocyclic or homocyclic, with two to eight linking atoms, and wherein either the linking atoms or a ring comprises an amino group and a carbonyl group; or a hydroxamate HDACi having the formula:

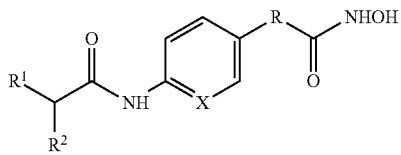

wherein R is a direct bond or an ethylene or ethenylene group, X is =CH— or =N—, $R^1$ is aryl or heteroaryl, and is mono- or bi-cyclic, and $R^2$ is straight or branched chain alkyl, optionally substituted by a mono- or bi-cyclic aryl or heteroaryl group.

Also provided is a method of treating a patient suspected of having a retroviral reservoir, comprising administering to said patient the arsenic-containing compound, which may also include administration of at least one further oxidative stress inducer, such as a non-iron metallodrug epigeneitic modulator, for instance gold-containing compounds, such as auranofin; a histone deacetylase inhibitor (HDACi); a pro-oxidant molecule, for instance a glutathione synthesis inhibitor such as BSO; and/or iron nitriloacetate or ferrous sulphate. Patients who are presenting low CD4 counts are preferred. Said patients may be undergoing, or have undergone, antiretroviral therapy (ART).

All aspects of the present invention may be used in the treatment of the latent reservoirs of retroviruses, which are present in every retroviral infection. The present invention may be used in the treatment of patients suspected of having latent reservoirs of retroviruses. Such retroviruses will be referred to herein as HIV-1, although it will be appreciated that this is for convenience, and that all such references include references to other retroviruses, unless otherwise apparent from the context.

The treatment is preferably intended to eliminate any latent reservoir of retrovirus. However, it will be appreciated that such treatments may also be used, less preferably, to control latent retrovirus. This may be advantageous where an individual is particularly susceptible to restart infections from the reservoirs, for example. The selective killing of latently infected cells described above is particularly advantageous.

A latent reservoir is a cell or cells containing the retrovirus either in quiescence, or replicating at low rates, such as less than 5% of the normal rate, such that the cell can act to protect the virus for a period of time, and often only releases viable virions weeks or months after normal antiretroviral treatment has stopped, thereby requiring continued treatment of the individual, when infection recurs through such a reservoir.

The 'normal' antiretroviral treatment referred to above, and which is administered to HIV-1-infected individuals, generally consists of a combination of at least three different drugs belonging to different classes, and are normally selected from the nucleosidic/nucleotidic reverse transcriptase inhibitors (NRTI's), the non-nucleosidic reverse transcriptase inhibitors (NNRTI's), and the protease inhibitors (PIs). A fusion inhibitor, or a chemokine receptor blocker may also form a part of the treatment. Recently, a further drug class, the integrase inhibitors, has been added to the arsenal of antiretroviral drugs. Antiretroviral drug combinations, in general, show the capacity to block ongoing viral replication, but have no potential for eradicating the virus from the body.

Reference herein is made to actives. It will be appreciated that this refers to the oxidative stress inducers, as discussed herein.

For the elimination of retroviral reservoirs, the treatment of the present invention uses the present actives, together with conventional anti-retroviral therapy, as well known in the art, and as described above, for example.

The actives may be administered direct to the patient in any suitable, pharmaceutically acceptable vehicle, and by any suitable route, as may be determined by a skilled person or physician. The actives may be administered orally, or as an injection or by transdermal patch, for example, and may be in free solution, or bound to a carrier. Other formulations, such as tablets, suppositories, creams and sprays will generally be less useful, although they may be used if deemed appropriate.

Suitable administration may be co-temporaneous or by separate delivery. Suitable vehicles may include targeted liposomes, bearing suitable antibodies, but infected latent cells are largely associated with the circulation, so administration by intravenous injection is also considered, although the preferred route of administration for all the compounds of the present invention is oral.

The present invention further provides a method for the selective elimination of latently infected cells, wherein the cells are latently infected by a lentivirus, especially HIV-1, said treatment comprising contacting said cells with an HDACi of the invention in combination with antiretroviral therapy.

Potentiation (synergy) has been shown between many of the compounds of the present inventions with HDACi's. This has the added advantage of reducing the amount of actives needed for treatment of the patient.

Furthermore, many of these actives have already been approved for human administration or have passed phase I clinical trials for safety.

Thus, the present invention further provides the use of the present actives in the treatment of a retroviral reservoir and for the selective elimination of latently infected cells.

Reference herein to BSO, Auranofin or Arsenic trioxide includes any analogues thereof.

It is also envisaged that glutathione synthesis inhibitors such as buthionine sulfoximine (BSO) can be used alone in the treatment of retroviral reservoirs, i.e. in treating latently infected cells, preferably by targeting and selectively kill infected, but not uninfected, cells.

Combinations of any of the oxidative stress inducers (non-iron metallodrug epigeneitic modulators), glutathione synthesis inhibitors or HDACi's described herein can be used.

The HDACi's are most preferably class I HDACi's. Those described in Mai et al 2009 are also preferred and its disclosure is hereby incorporate by reference.

The following Experimental section is for illustration only, and is not limiting on the present invention.

All references cited herein are hereby incorporated by reference to the extent that they do not conflict with the teaching of the present invention.

EXAMPLE 1

Auranofin

Methods

HIV-1 induction in ACH-2 and U1 cells. Latently HIV-1 infected ACH-2 cells were incubated with the compounds in 96-well plates under standard culture conditions (RPMI medium, 10% foetal bovine serum/FBS, and proper antibiotics, which were switched from time to time in order to avoid selection of drug resistant contaminating bacteria), and the content of HIV-1 p24 core antigen in supernatants was measured at 24 and 72 h of incubation by HIV-1 p24 ELISA kits (Perkin Elmers, Boston, Mass.), following the Manufacturer's instructions. Cell viability was tested for each treatment after collection of supernatants, as follows.

Cell viability assay. Cell viability was quantitated using the methyl tetrazolium (MTT) procedure. Absorbance values were generated at a wavelength of 550 nm using 96-well ELISA readers and subtracted of the blank values using cell culture media in the absence of cells. Cell viability in the presence of the test compounds was expressed as a percentage of the cell viability of control untreated cell cultures.

Test for detection of the combined effects of two drugs. For detection of synergism/antagonism/additivity, cells were incubated with different concentrations of either drug alone or both drugs in combination, and, again, viral replication was quantified at three days of incubation by ELISA testing.

Flow cytometry. To determine the HIV-1 LTR-controlled expression of green fluorescent protein (GFP) in the Jurkat cell clones, cells were pooled and washed three times in ice-cold PBS with $NaN_3$ (0.02%) and bovine serum albumin (2%; PBS A/A). Cells were then fixed in 1% paraformaldehyde for 20 min., washed and resuspended in PBS A/A. Fluorescence was then acquired by a flow cytometer (FACScalibur, Becton-Dickinson, Mountain View, Calif.). Fluorescence data were collected on a 4-decade log scale and the relative fluorescence intensity was stated as the percentage of fluorescent cells beyond the threshold value established using non-transfected Jurkat cells.

Detection of NF-kappaB nuclear translocation. Nuclear extracts from control Jurkat 8.4 cells and cells treated with auranofin at different times of incubation were obtained using a nuclear extraction kit (Chemicon International), following the Manufacturer's instructions. NF-kappaB nuclear translocation was detected using a colorimetric transcription factor assay (Millipore) for the p65 subunit. Results were expressed as a percentage of the signal obtained in cells incubated with the potent NF-kappaB stimulating cytokine TNF-alpha (5 ng/ml) for 1.5 h, at which the peak of nuclear translocation of NF-kappaB is reached.

Data analysis. Experiments were performed on, at least, two different occasions with similar results and results were shown as means. Analyses were conducted using the Graph-Pad software. For concentration-dependence curves, the percentage-of-control values were plotted against the different drug concentrations. An appropriate transformation was applied to restore normality where necessary. The lines, or curves, best fitting the data points were generated by the least squares method. The threshold for significance was considered to be P=0.05, in case of linear regression, or $R^2$=0.7, in case of non-linear regression. Non-linear regression was preferred over linear regression (also in case the latter was significant), where the $R^2$ was superior. Differences between drug concentration responses were analyzed using the t-test for slope.

Synergism was analyzed by means of percentage-of-synergism values, which represent the percent difference between the effects of the drug combination and the sum of the effects of either drug administered separately at matched concentrations, calculated as follows:

$$PS = 100 \cdot [E_{drug\ A+drug\ B} - (E_{drug\ A} + E_{drug\ B})] / (E_{drug\ A} + E_{drug\ B})$$

where PS is the percentage of synergism and E is the effect of the drug, expressed as the fold-increase in p24 production.

Three-dimensional (3D) x,y,z graphs were generated by plotting percentage of synergism values (z axis) against the matched drug concentrations used (in the x and y axes). 3D surfaces were generated using Microsoft Excel. Highly convex surfaces indicate synergism. Flat surfaces indicate an additive effect, while concave surfaces show antagonism.

Results

HIV-1 Activation by Auranofin in U1 and ACH-2 Cells

To preliminarily assess the HIV-1 activating effects of auranofin in cell lines in which the post-integrational stages of HIV-1 replication are inducible, HIV-1 infected T-lymphoid ACH-2 and monocytic U1 cells were incubated with increasing concentrations of the compound, and HIV-1 replication was measured at 24 h (data not shown) and 72 h of incubation (FIG. 2 shows data from ACH-2 cells). 5 ng/ml of TNF-alpha, a cytokine potently promoting HIV-1 replication by inducing NF-kappaB (p65/p50) activation was used as a positive control. Results showed that auranofin increased HIV-1 replication in a time- and dose-dependent manner (P=0.0295, t-test for regression; FIG. 5B) in the 0.125-0.5 µM range of concentrations, approximating the mean plasma levels observed during treatment of rheumatoid arthritis [Benn et al., 1991].

Of note, the HIV-1 activating effect of auranofin was synergistic to that of MC2113, a class I HDACI from our institutional library endowed with poor toxicity [Rotili et al., 2009]. This was shown in experiments in which auranofin was co-administered with MC 2113 to U1 cells (FIG. 3). The effect was visible as soon as at 24 h of incubation.

The Cellular Basis for the Auranofin Response

To evaluate the auranofin response within a cellular population, we used the latently infected T-lymphoid Jurkat cell clone 8.4, established by Jordan et al. [Jordan et al., 2003]. This cell clone contains the entire HIV-1 genome under control of the LTR and presenting the GFP gene replacing nef. As opposed to U1 cells, these cells display non-significant basal levels of HIV-1 expression and have a functional Tat/TAR axis. In the 8.4 cells, auranofin induced a dose-dependent shift in fluorescence (FIG. 4), which was evident mostly at the highest concentrations adopted. The cellular basis for the additive effects of the HDACI/auranofin combination was also explored. We found that addition of auranofin recruited the HDACi-unresponsive cells into the responding cell population (FIG. 5).

Similar results were obtained in other cell lines expressing GFP under control of HIV-1 LTR and using other HDACi such as suberoylanilide hydroxamic acid (SAHA). Jurkat A1 cells have a green fluorescent protein (GFP) gene under control of HIV-1 LTR, which is quiescent in a portion of the cell population. These cells were treated with a clinically relevant concentration of auranofin (0.25 µM) or 1 µM of MC2113, or both. Data was presented as the percentage of fluorescent cells beyond a threshold established using non-GFP expressing Jurkat cells. This data demonstrated induction of LTR-controlled expression of green-fluorescent protein (GFP) by auranofin and a non-class-specific histone deacetylase inhibitor (SAHA).

Auranofin-Induced NF-kappaB Nuclear Translocation

It is well known that oxidative stress causes activation and nuclear localization of the NF-kappaB heterodimer Rel A (p65)/p50 [Rahman et al., 2004], which is important for HIV-1 transcription and replication [Williams et al., 2007]. If auranofin should activate HIV-1 from quiescence by inducing an oxidative stress within target cells, then, NF-kappa B (p65/p50) nuclear translocation should be visible. To test this hypothesis, aliquots of nuclear extracts from Jurkat 8.4 cells treated with auranofin (250 µM) were subjected to a colorimetric assay for the p65 (RelA) subunit of NF-kappaB. Results showed a time-dependent NF-kappaB accumulation within the nuclei (FIG. 6). We conclude that auranofin induces NF-kappaB (p65/p50) activation under conditions similar to those at which it activates HIV-1 from quiescence.

Synergistic Effects of Auranofin with Other Pro-Oxidant Strategies

To gain some insight into the auranofin-induced HIV-1 activation from quiescence, the effects of the drug were tested in the presence of some well-characterized pro-oxidant molecules, i.e., iron nitriloacetate (FeNTA) [Savarino et al., 1999], which promotes oxidative stress through the Fenton reaction, and buthionine sulfoximine (BSO), an irreversible inhibitor of gamma-glutamyl cysteine synthetase, a limiting enzyme in the glutathione synthetic pathway [Anderson, 1998]. Results showed that, similarly to auranofin, FeNTA dose-dependently induced HIV-1 replication in ACH-2 cells (data not shown), whereas BSO alone had no effect on HIV-1 inducing effects at concentrations up to 500 µM (data not shown). When co-administered with either of the two agents, auranofin exerted synergistic HIV-1 activating effects, as shown by the highly convex surfaces in the percentage-of-synergism graphs (FIGS. 7 and 8). We conclude that auranofin potentiates iron-induced HIV-1 activation and that the effects of this drug are enhanced by glutathione depletion.

REFERENCES (all references cited herein are hereby incorporated to the extent that they do not conflict with the present invention).

Anderson M E: Glutathione: an overview of biosynthesis and modulation. Chem Biol Interact 1998, 111-112:1-14.

Benn H P, Schnier C, Bauer E, Seiler K U, Elhöft H, Löffler H. Biliary, renal and fecal elimination and distribution of gold after a single oral administration of auranofin, quantified by the instrumental neutron activation analysis method. Z Rheumatol. 1991 January-February; 50(1):32-8.

Chouchane S, Snow E T. In vitro effect of arsenical compounds on glutathione-related enzymes. Chem Res Toxicol. 2001 May; 14(5):517-22.

Daniel L W, Civoli F, Rogers M A, Smitherman P K, Raju P A, Roederer M. ET-18-OCH3 inhibits nuclear factor-kappa B activation by 12-O-tetradecanoylphorbol-13-acetate but not by tumor necrosis factor-alpha or interleukin 1 alpha. Cancer Res. 1995 Nov. 1; 55(21):4844-9.22. Chircorian A, Barrios A M, Inhibition of lysosomal cysteine proteases by chrysotherapeutic compounds: a possible mechanism for the antiarthritic activity of Au(I), Bioorg. Med. Chem. Lett. 14 (2004), pp. 5113-5116.

Demonté D, Quivy V, Colette Y, Van Lint C: Administration of HDAC inhibitors to reactivate HIV-1 expression in latent cellular reservoirs: implications for the development of therapeutic strategies. Biochem Pharmacol 2004, 68:1231-1238.

Dueñas-González A, Garcia-López P, Herrera L A, Medina-Franco J L, González-Fierro A, Candelaria M. The prince and the pauper. A tale of anticancer targeted agents. Mol Cancer. 2008 Oct. 23; 7:82.

Duverger A, Jones J, May J, Bibollet-Ruche F, Wagner F A, Cron R Q, Kutsch O: Determinants of the establishment of human immunodeficiency virus type 1 latency. J Virol 2009, 83:3078-93.

Hamer D H: Can HIV be Cured? Mechanisms of HIV persistence and strategies to combat it. Curr HIV Res. 2004, 2:99-111.

Huang R, Wallqvist A, Covell D G. Anticancer metal compounds in NCI's tumor-screening database: putative mode of action. Biochem Pharmacol. 2005 Apr. 1; 69(7):1009-39.

Israël N, Gougerot-Pocidalo M A: Oxidative stress in human immunodeficiency virus infection. Cell Mol Life Sci 1997, 53:864-70.

Jeon K I, Jeong J Y, Jue D M. Thiol-reactive metal compounds inhibit NF-kappa B activation by blocking I kappa B kinase. J. Immunol. 2000 Jun. 1; 164(11):5981-9.

Jordan A, Bisgrove D, Verdin E: HIV reproducibly establishes a latent infection after acute infection of T cells in vitro. EMBO J. 2003, 22:1868-77.

Kalantari P, Narayan V, Natarajan S K, Muralidhar K, Gandhi U H, Vunta H, Henderson A J, Prabhu K S. Thioredoxin reductase-1 negatively regulates HIV-1 transactivating protein Tat-dependent transcription in human macrophages. J Biol. Chem. 2008 Nov. 28; 283(48):33183-90.

Lu J, Chew E H, Holmgren A. Targeting thioredoxin reductase is a basis for cancer therapy by arsenic trioxide. Proc Natl Acad Sci USA. 2007

Lu J, Holmgren A. Selenoproteins. J Biol. Chem. 2009 Jan. 9; 284(2):723-7.

Omata Y, Folan M, Shaw M, Messer R L, Lockwood P E, Hobbs D, Bouillaguet S, Sano H, Lewis J B, Wataha J C. Sublethal concentrations of diverse gold compounds inhibit mammalian cytosolic thioredoxin reductase (TrxR1). Toxicol In Vitro. 2006 September; 20(6):882-90.

Patai S. The Chemistry of Organic Derivatives of Gold and Silver. Edited by Saul Patai and Zvi Rappoport 1999 John Wiley & Sons, Ltd., passim.

Rahman I, Marwick J, Kirkham P: Redox modulation of chromatin remodeling: impact on histone acetylation and deacetylation, NF-kappaB and pro-inflammatory gene expression. Biochem Pharmacol 2004, 68:1255-67.

Rigobello M P, Scutari G, Boscolo R, Bindoli A. Induction of mitochondrial permeability transition by auranofin, a gold (I)-phosphine derivative. Br J. Pharmacol. 2002 August; 136(8):1162-8.

Rigobello M P, Scutari G, Folda A, Bindoli A. Mitochondrial thioredoxin reductase inhibition by gold(I) compounds and concurrent stimulation of permeability transition and release of cytochrome c. Biochem Pharmacol. 2004 Feb. 15; 67(4):689-96.

Rotili D, Simonetti G, Savarino A, Palamara A T, Migliaccio A R, Mai A: Non-cancer uses of histone deacetylase inhibitors: effects on infectious diseases and β-hemoglobinopathies. Curr Topics Med Chem 2009, 9(3):272-91.

Sannella A R, Casini A, Gabbiani C, Messori L, Bilia A R, Vincieri F F, Majori G, Severini C. New uses for old drugs. Auranofin, a clinically established antiarthritic metallodrug, exhibits potent antimalarial effects in vitro: Mechanistic and pharmacological implications. FEBS Lett. 2008 Mar. 19; 582(6):844-7.

Savarino A, Bottarel F, Malavasi F, Dianzani U. Role of CD38 in HIV-1 infection: an epiphenomenon of T-cell activation or an active player in virus/host interactions? AIDS. 2000 Jun. 16; 14(9):1079-89.

Savarino A, Cauda R, Cassone A. On the use of chloroquine for chikungunya. Lancet Infect Dis. 2007 October; 7(10):633.

Savarino A, Lucia M B, Giordano F, Cauda R. Risks and benefits of chloroquine use in anticancer strategies. Lancet Oncol. 2006 October; 7(10):792-3. No abstract available.

Savarino A, Pescarmona G P, Boelaert J R: Iron metabolism and HIV infection: reciprocal interactions with potentially harmful consequences? Cell Biochem Funct 1999, 17:279-87.

Traber K E, Okamoto H, Kurono C, Baba M, Saliou C, Soji T, Packer L, Okamoto T. Anti-rheumatic compound aurothioglucose inhibits tumor necrosis factor-alpha-induced HIV-1 replication in latently infected OM10.1 and Ach2 cells. Int Immunol. 1999 February; 11(2):143-50.

Williams S A, Greene W C: Regulation of HIV-1 latency by T-cell activation. Cytokine 2007, 39:63-74.

Wu Y. HIV-1 gene expression: lessons from provirus and non-integrated DNA. Retrovirology 2004, 1:13 (25 Jun. 2004).

EXAMPLE 2

HDACi's

HIV-1 infected lymphocytic ACH-2 and monocytoid U1 cells (both displaying low baseline levels of HIV-1 replication) are well established cell-line models for HIV-1 latency [Munier et al., 2005]. They were incubated with the test compounds in 96-well plates under standard culture conditions, and HIV-1 replication was measured at 72 h of incubation by ELISA testing. The potency of the compounds on HIV-1 induction was assessed as the fold-increase in HIV-1 replication in the presence of a standard concentration of 1 µM of the test compound (this concentration is generally used as a threshold for lead compounds selection), as compared to the baseline levels observed in untreated controls. We found several compounds capable of inducing HIV-1 replication in latently infected cells, and, in general, there was good agreement between results in ACH-2 and U1 cells.

Several compounds (Class I selective or non-selective HDACi) showed remarkable HIV-1 stimulatory activity (Table 1), which correlated with infected cell killing (U1 cells: P=0.0378; ACH-2 cells: P=0.0017; Spearman's non-parametric test (FIG. 9 A,B)). Class I selective compounds, in general, showed lower toxicity than non-selective compounds (data not shown). Moreover, some Class I-selective HDACi promoting HIV-1 reactivation induced selective killing of HIV-1-infected cells. This is exemplified by data using MC1855 (P<0.01; t-test for slope; FIG. 9 C,D).

From the structure/activity relationships, particular requirements emerge for efficient induction of HIV-1 escape from latency. In general, HDACi display a general pharmacophoric model, which comprises a cap group (CAP) able to interact with the rim of the catalytic tunnel, often with a polar connection unit (CU), linking the CAP to a hydrophobic spacer (HS), which allows the molecule to lie into the tunnel [Mai et al., 2005b]. Finally, the HS carries at the end a $Zn^{2+}$ binding group (ZBG) that is able to complex the $Zn^{2+}$ at the bottom of the cavity [Mai et al., 2005b]. Generally the ZBG consists of a hydroxamate, carboxylate, or a benzamide. MS 275 is a Class-I selective HDACi in clinical trials for cancer treatment [Nishioka et al., 2008; Hauschild et al., 2008]. This compound proved the most potent inducer of HIV-1 escape from latency among the compounds tested, displaying activity in the nanomolar range in ACH-2 (FIG. 10) and U1 cells (not shown), well within the plasma concentrations achievable in vivo [Zhao et al., 2007]. Our SAR studies are not intended to limit the chemical types of HADACi administrable with butionine sulfoximine (BSO), and synergistic effects (see below) of HDACi with BSO are extendable to the entire HDACi class.

BSO which induces oxidative stress, was also tested. BSO, an inhibitor of gamma glutamyl cysteine synthetase [Garaci et al., 1996] (a limiting enzyme in glutathione synthesis), promotes oxidative stress indirectly by decreasing the cellular antioxidant defence [Anderson, 1998]. This compound was tested because it might favour NF-kappa B activation, which is enhanced in an oxidative environment. Results showed that BSO did not significantly induce HIV-1 replication in either ACH-2 or U1 cells (data not shown). Despite this, BSO was tested to determine whether it might potentiate the effects of HDACi. Results showed that BSO strikingly increased the HIV-1 promoting effects of two benzamide HDACi, i.e. MS 275 and MC2211, as shown in FIGS. 11 and 12. The highly convex 3D surfaces of the percentage-of-synergism graph in ACH-2 cells point to a synergistic effect of the drug combinations. The BSO concentrations showing the synergistic effect are achievable therapeutically [Lacreta et al., 1994]. Similar results were obtained in U1 cells (data not shown).

The finding that Class I HDAC inhibition is per se sufficient for HIV-1 reactivation is particularly advantageous.

Methods

Chemistry. Melting points were determined on a Buchi 530 melting point apparatus and are uncorrected. Infrared (IR) spectra (KBr) were recorded on a Perkin-Elmer Spectrum One instrument. $^1H$ NMR spectra were recorded at 400 MHz on a Bruker AC 400 spectrometer; chemical shifts are reported in $\delta$(ppm) units relative to the internal reference, tetramethylsilane ($Me_4Si$). All compounds were routinely checked by TLC and $^1H$ NMR. TLC was performed on aluminium-backed silica gel plates (Merck D C, Alufolien Kieselgel 60 $F_{254}$) with spots visualised by UV light. All solvents were reagent grade and, when necessary, were purified and dried by standard methods. The concentration of solutions after reactions and extractions involved the use of a rotary evaporator operating at reduced pressure of ca. 20 Torr. Organic solutions were dried over anhydrous sodium sulphate. Analytical results are within ±0.40% of the theoretical values. A SAHA sample for biological assays was prepared as well according to standard methods. All chemicals were purchased from Aldrich Chimica, Milan (Italy) or from Lancaster Synthesis GmbH, Milan (Italy) and were of the highest purity [Mai et al. 2006].

General Procedure for the Synthesis of Ethyl Esters of 4-(3,4-Dihydro-4-oxo-6-substituted-2-pyrimidinylthio)methylcinnamic Acids. Example: Ethyl Ester of 4-(3,4-Dihydro-4-oxo-6-benzyl-2-pyrimidinylthio)methylcinnamic Acid. A mixture of 6-benzyl-4-hydroxy-2-mercaptopyrimidine (6.87 mmol, 1.5 g), crude ethyl 4-bromomethylcinnamate (7.56 mmol, 2.2 g), and anhydrous potassium carbonate (7.56 mmol, 1.0 g) in 3 mL of anhydrous DMF was stirred at room temperature for 1 h. After treatment with cold water (100 mL), the aqueous phase was extracted with ethyl acetate (3 40 mL). The organic phase was washed with brine (3 40 mL), dried, and evaporated to dryness to furnish the crude desired compound, which was purified by chromatography on a silica gel column, eluting with a mixture ethyl acetate/hexane (1:1) to give the desired product as a white solid (1.2 g). $^1$H NMR (CDCl$_3$) δ1.33 (t, 3H, CH$_2$CH$_3$), 3.83 (s, 2H, PhCH$_2$), 4.26 (q, 2H, CH$_2$CH$_3$), 4.38 (s, 2H, CH$_2$S), 5.98 (s, 1H, C$_5$—H), 6.40 (d, 1H, CH=CHCO), 7.33 (m, 9H, two benzene rings), 7.61 (d, 1H, CH=CHCO), 13.20 (s, 1H, NH). Anal. C, H, N, S [Mai et al., 2006].

General Procedure for the Synthesis of 6-(3,4-Dihydro-4-oxo-6-(un)substituted-2-pyrimidinylthio)-hexanoic Acids and 4-(3,4-Dihydro-6-substituted-4-oxopyrimidin-2-ylthio)methylcinnamic Acids. Example: 6-(3,4-Dihydro-4-oxopyrimidin-2-ylthio)hexanoic Acid. A mixture of the appropriate ethyl ester (1.1 mmol, 0.3 g), 2 N KOH (8.8 mmol, 0.49 g), and EtOH (5 mL) was stirred at room temperature for 18 h. The solution was poured into water (50 mL) and extracted with ethyl acetate (2 20 mL). HCl (2 N) was added to the aqueous layer until the pH 5, and the precipitate was filtered and recrystallised to yield the title compound (0.23 g) as a pure solid. $^1$H NMR (DMSO-d$_6$) δ1.32 (m, 2H, CH$_2$CH$_2$CH$_2$S), 1.49 (m, 2H, CH$_2$CH$_2$CO), 1.61 (m, 2H, CH$_2$CH$_2$S), 1.93 (t, 2H, CH$_2$CO), 3.06 (t, 2H, CH$_2$S), 6.07 (s, 1H, C$_5$—H), 7.83 (s, 1H, C$_6$—H), 12.2 (s, 1H, COOH). Anal. C, H, N, S [Mai et al. 2006].

General Procedure for the Synthesis of N-Hydroxy-6-(3,4-dihydro-4-oxo-6-(un)substituted-2-pyrimidinylthio)hexanamides and N-Hydroxy-4-(3,4-dihydro-6-substituted-4-oxopyrimidin-2-ylthio)-methylcinnamylamides. Example: N-Hydroxy-6-(3,4-dihydro-4-oxopyrimidin-2-ylthio)hexanamide. To a 0° C. cooled solution of the appropriate carboxylic acid (0.9 mmol, 0.22 g) in dry tetrahydrofuran (5 mL), ethyl chloroformate (2.2 mmol, 0.21 mL) and triethylamine (2.3 mmol, 0.33 mL) were added, and the mixture was stirred for 10 min. The solid was filtered off, and to the filtrate was added O-(2-methoxy-2-propyl)hydroxylamine (5.4 mmol, 0.4 mL). The resulting mixture was stirred at room temperature for 1 h, then it was evaporated under reduced pressure, and the residue was diluted in MeOH (5 mL). Amberlyst 15 ion-exchange resin (0.18 g) was added to the solution of the O-protected hydroxamate, and the mixture was stirred at room temperature for 1 h. Afterward, the reaction was filtered, and the filtrate was concentrated in a vacuum to give crude final product, which was purified by crystallization. $^1$H NMR (DMSO-d$_6$) δ1.30 (m, 2H, CH$_2$CH$_2$CH$_2$S), 1.46 (m, 2H, CH$_2$CH$_2$CO), 1.60 (m, 2H, CH$_2$CH$_2$S), 1.90 (t, 2H, CH$_2$CO), 3.02 (t, 2H, CH$_2$S), 6.10 (s, 1H, C$_5$—H), 7.85 (s, 1H, C$_6$—H), 8.66 (s, 1H, NHOH), 10.33 (s, 1H, NHOH), 12.5 (s, 1H, uracil NH). Anal. C, H, N, S [Mai et al., 2006].

General procedure for the synthesis of 3-(4-acylaminophenyl)-N-hydroxy-2-propenamides. Example: 3-[4-(2,3-Diphenylpropionylamino)phenyl]-N-hydroxy-2-propenamide (MC1895).

Ethyl chloroformate (1.26 mmol, 0.12 mL) and triethylamine (1.37 mmol, 0.19 mL) were added to a cooled (0° C.) solution of 3-[4-(2,3-Diphenylpropionylamino)phenyl]-2-propenoic acid (1.05 mmol, 0.39 g) in dry THF (10 mL), and the mixture was stirred for 10 min. The solid was filtered off, and O-(2-methoxy-2-propyl)hydroxylamine (3.15 mmol, 0.23 mL) was added to the filtrate. The solution was stirred for 15 min at 0° C., then was evaporated under reduced pressure, and the residue was diluted in methanol (10 mL). Amberlyst® 15 ion-exchange resin (105 mg) was added to the solution of the O-protected hydroxamate, and the mixture was stirred at room temperature for 1 h. After, the reaction was filtered and the filtrate was concentrated in vacuo to give the crude MC1895 which was purified by crystallization. $^1$H NMR (DMSO-d$_6$) δ 3.05 (m, 1H, PhCH$_2$), δ 3.60 (m, 1H, PhCH$_2$), δ 3.75 (m, 1H, PhCHCO), δ 6.36 (d, 1H, PhCH=CHCOOEt), δ 7.15-7.70 (m, 15H, benzene protons and PhCH=CHCOOEt), δ 9.00 (s, 1H, OH), δ 10.23 (s, 1H, CONHPh), δ 10.85 (s, 1H, NHOH). Anal. C, H, N, O.

Maize HD2, HD1-B, and HD1-A Enzyme Inhibition in Vitro. Radioactively labelled chicken core histones were used as the enzyme substrate according to established procedures [referenced in: Mai et al., 2006]. The enzyme liberated tritiated acetic acid from the substrate, which was quantified by scintillation counting. The IC$_{50}$ values are the results of triple determinations. A 50 µL sample of maize enzyme (at 30° C.) was incubated (30 min) with 10 microL of total [$^3$H]acetate-prelabelled chicken reticulocyte histones (2 mg/mL). The reaction was stopped by the addition of 36 microL of 1 M HCl/0.4 M acetate and 800 microL of ethyl acetate. After centrifugation (10 000 g, 5 min), an aliquot of 600 microL of the upper phase was counted for radioactivity in 3 mL of liquid scintillation cocktail. The compounds were tested at a starting concentration of 40 microM, and active substances were diluted further. TSA and SAHA were used as the reference compounds, and blank solvents were used as negative controls [Mai et al. 2006].

Mouse HDAC1 Enzyme Assay. For the inhibition assay, partially purified HDAC1 from mouse liver (anion exchange chromatography) was used as the enzyme source. HDAC activity was determined using [$^3$H]acetate-prelabelled chicken reticulocyte histones as the substrate. Mouse HDAC1 (50 microL) was incubated with different concentrations of compounds for 15 min on ice, and 10 µL of total [$^3$H]acetate-prelabelled chicken reticulocyte histones (2 mg/mL) were added, resulting in a concentration of 41 microM. The mixture was incubated at 37° C. for 1 h. The reaction was stopped by the addition of 50 microL of 1 M HCl/0.4 M acetylacetate and 1 mL ethyl acetate. After centrifugation at 10 000 g for 5 min, an aliquot of 600 microL of the upper phase was counted for radioactivity in a 3 mL liquid scintillation cocktail [Mai et al., 2006].

Cellular Assays. Cell Lines and Cultures. The U937 cell line was cultured in RPMI with 10% foetal calf serum, 100 U/mL of penicillin, 100 microg/mL of streptomycin, and 250 ng/mL of amphotericin-B, 10 mM HEPES and 2 mM glutamine. U937 cells were kept at the constant concentration of 200 000 cells per milliliter of culture medium. Human breast cancer ZR-75.1 cells were propagated in DMEM medium supplemented with 10% foetal calf serum and antibiotics (100 U/mL of penicillin, 100 micrograms/mL of streptomycin, and 250 ng/mL of amphotericin-B).

Ligands and Materials. SAHA was dissolved in DMSO and used at 1 or 5 microM. MS-275 (gift from Schering A G) was dissolved in ethanol and used at 5 microM. UBHA compounds 1d and 1j were dissolved in DMSO and used at 1 or 5 microM.

Cell-Based Human HDAC1 and HDAC4 Assays. Cells (U937 cells for the HDAC1 assay and ZR75.1 cells for the HDAC4 assay) were lysed in IP buffer (50 mM Tris-HCl at pH 7.0, 180 mM NaCl, 0.15% NP-40, 10% glycerol, 1.5 mM $MgCl_2$, 1 mM $NaMO_4$, and 0.5 mM NaF) with a protease inhibitor cocktail (Sigma), 1 mM DTT, and 0.2 mM PMSF for 10 min in ice and centrifuged at 13 000 rpm for 30 min. Then, 1000 micrograms of extracts were diluted in IP buffer up to 1 mL and pre-cleared by incubating with 20 microL of A/G plus Agarose (Santa Cruz) for 30 min to 1 h on a rocking table at 4° C. Supernatants were transferred into a new tube, and the antibodies (around 3 to 4 µg) were added and IP was allowed to proceed overnight at 4° C. on a rocking table. The antibodies used were HDAC1 (Abcam) and HDAC4 (Sigma). As the negative control, the same amount of protein extracts were immunoprecipitated with the corresponding purified IgG (Santa Cruz). On the next day, 20 microL of A/G and Agarose (Santa Cruz) were added to each IP, and incubation was continued for 2 h. The beads were recovered by brief centrifugation and washed with cold IP buffer several times. The samples were than washed twice in PBS and re-suspended in 20 microL of sterile PBS. The HDAC assay was carried out according to the supplier's instructions (Upstate). Briefly, samples immunoprecipitated with the HDAC4 and HDAC1 or with purified IgG were pooled separately to homogenise all samples. Then, 10 microL of the IP was incubated with a previously labelled $^3$H-Histone H4 peptide linked with streptavidine agarose beads (Upstate). In detail, 120 000 CPM of the H4-$^3$H-acetyl-peptide was used for each tube and incubated in 1 HDAC buffer with 10 microL of the sample in the presence or absence of HDAC inhibitors with a final volume of 200 µL. Those samples were incubated overnight at 37° C. in slow rotation. On the next day, 50 µL of a quenching solution was added, and 100 microL of the samples were counted in duplicate after brief centrifugation in a scintillation counter. Experiments have been carried out in quadruplicate [Mai et al., 2006].

Compound preservation. Compounds were preserved as dry powders, and resuspended in dimethyl sulphoxide (DMSO) at the moment of use. Initial concentrations in DMSO solutions were adjusted in order to obtain proper drug concentrations with less than 2/1000 DMSO (v/v) in the final cell culture media.

HIV-1 reactivation screening test. Latently HIV-1 infected ACH-2 cells were incubated with the compounds in 96-well plates under standard culture conditions (RPMI medium, 10% foetal bovine serum/FBS, and proper antibiotics, changed from time to time in order to avoid selection of drug resistant contaminating bacteria), and the content of HIV-1 p24 core antigen in supernatants was measured at 72 h of incubation by HIV-1 p24 ELISA kits (from Perkin Elmer), following the Manufacturer's instructions. The potency of the compounds on induction of HIV-1 escape from latency was assessed as the fold-increase (%) in HIV-1 replication in the presence of a standard concentration of 1 microM, as compared to the baseline levels observed in untreated controls. The 1 µM concentration was chosen because it is generally considered to be a threshold for selection of lead compounds. Cell viability was tested for each treatment after collection of supernatants, as follows.

Cell viability assay. Cell viability was quantitated using the highly standardised methyl tetrazolium (MTT) procedure (described in detail in: Savarino A, Calosso L, Piragino A, Martini C, Gennero L, Pescarmona G P, Pugliese A. Modulation of surface transferrin receptors in lymphoid cells de novo infected with human immunodeficiency virus type-1. Cell Biochem Funct. 1999 March; 17(1):47-55). Absorbance values were generated at a wavelength of 450 nm using 96-well ELISA readers and subtracted of the blank values using cell culture media in the absence of cells. Cell viability in the presence of the test compounds was expressed as a percentage of the cell viability of control untreated cell cultures. For testing of selective killing, Non-infected H9, and U937, and HIV-1 infected $H_{IIIB}$, ACH-2, and U1 cells were incubated with the test compounds for seven days, and cell viability was measured as described above.

Concentration-response curves. Concentration-response curves were generated for those compounds with the best activities, by incubating cells with decreasing concentrations of the compounds (0.001-1 µM).

Test for detection of combined drug effects. For detection of synergy/antagonism, cells were incubated with different combinations of BSO alone, the histone deacetylase inhibitor alone, or both, and, again, viral replication was quantified at three days of incubation by ELISA testing.

Data analysis. Experiments were performed on at least two different occasions with similar results and results were shown as means. Analyses were conducted using the Graph-Pad software. Correlation between cell death/HIV-1 reactivation was assessed by plotting, for each compound, the percentage of inhibition of cell viability against the fold-increase in HIV-1 replication. Significance of the correlation was assessed using Spearman's correlation coefficients using a significance threshold of P=0.05. For concentration-dependence curves, the fold-increase values were plotted against the different concentrations. An appropriate transformation was applied to restore normality where necessary. The lines, or curves, best fitting the data points were generated by the least squares method. The threshold for significance was considered to be P=0.05, in case of linear regression, or $R^2=0.7$, in case of non-linear regression. Synergism was analysed by means of percentage-of-synergism values, which represent the percent difference between the effects of the drug combination and the sum of the effects of the histone deacetylase inhibitor and the pro-oxidant drug administered separately at matched concentrations, calculated as follows:

$$PS=100 \cdot [E_{drug\ A+drug\ B}-(E_{drug\ A}+E_{drug\ B})]/(E_{drug\ A}+E_{drug\ B})$$

where PS is the percentage of synergism and E is the effect of the drug concentration, expressed as the fold-increase in p24 production.

Three-dimensional (3D) x,y,z graphs were generated by plotting percentage of synergism values (z axis) against the matched drug concentrations used (in the x and y axes). 3D surfaces were generated using Microsoft Excel. Highly convex surfaces indicate synergism. Flat surfaces indicate an additive effect, while concave surfaces show antagonism.

TABLE 1

Structures and potencies of different compounds in inducing HIV-1 replication in lymphocytic ACH-2 and monocytoid U1 cells.

| Compound | Structure | HDACs inhibited | Chemical class | Fold increase (%) in HIV-1 p24 at 1 μM (unless otherwise specified) ACH-2 cells | U1 cells |
|---|---|---|---|---|---|
| MC 1855 | (structure) | Class 1 | Hydroxamates | 699 | 817 |
| MC 2111 | (structure) | Class 1 | Hydroxamates | 2.460 | 2.960 |
| MC 2113 | (structure) | Class 1 | Hydroxamates | 3.304 | 2.846 |
| MC 2195 | (structure) | Class 1 | Hydroxamates | 3.427 | 4.076 |
| MC 1895 | (structure) | Class 1 | Hydroxamates | 2.981 | 3.747 |

TABLE 1-continued

Structures and potencies of different compounds in inducing HIV-1 replication in lymphocytic ACH-2 and monocytoid U1 cells.

| Compound | Structure | HDACs inhibited | Chemical class | Fold increase (%) in HIV-1 p24 at 1 µM (unless otherwise specified) ACH-2 cells | U1 cells |
|---|---|---|---|---|---|
| MC 1857 | (structure) | NS | Hydroxamates | 1.655. | 880 |
| MC 1864 | (structure) | NS | Hydroxamates | 1.145 | 995 |
| MC 275 | (structure) | Class 1 | Benzamides | 23.162 | 1.835 |
| MC 211 | (structure) | Class 1 | Benzamides | 2.025 | 4.811 |

TABLE 2

HDAC inhibiting activity of cited MC compounds.

| Compound | Ref. | IC$_{50}$ values, nM | | | % inhibition @ 5 µM | |
|---|---|---|---|---|---|---|
| | | Maize HD1-B | Maize HD1-A | mouse HDAC1 | IP HDAC1 | IP HDAC4 |
| MC1855 | | 162 | 55 | 128 | 78.7 | 0 |
| MC2111 | | 58 | 42 | 620 | 73.6 | 0 |
| MC2113 | | 62 | 69 | 560 | 64.9 | 22.4 |
| MC2195 | | 11 | 8 | 69 | 46.7 | 93.1 |
| MC2211* | Mai et al., 2008 | | | | | |
| MC1857 | | 72 | 80 | 291 | 79.3 | N.D. |
| MC1864 | | 89 | 64 | 305 | 55.0 | 60.4 |
| MC1895 | | 133 | 74 | 83 | 72.5 | 16.1 |
| MS 275** | | | | | 65.4 | 0 |

N.D., Not determined
*tested on human recombinant HDAC1 and 4.
**confirmed by literature data using tested on human recombinant HDACs.

REFERENCES FOR HDACI'S

Anderson M E. Glutathione: an overview of biosynthesis and modulation. Chem Biol Interact. 1998 Apr. 24; 111-112:1-14.

Annemieke J. M. de Ruijter, Albert H. Van Gennip, Huib N. Caron et all. Histone deacetylases (HDACs): Characterization of the classical HDAC family. Biochem. J. 2003. 370, 737-749.

Benn H P, Schnier C, Bauer E, Seiler K U, Elhöft H, Löffler H.[Biliary, renal and fecal elimination and distribution of gold after a single oral administration of auranofin, quantified by the instrumental neutron activation analysis method]Z Rheumatol. 1991 January-February; 50(1):32-8.

Biochem J. 2008 Jan. 15; 409(2):581-9.

Bowie A, O'Neill L A. Oxidative stress and nuclear factor-kappaB activation: a reassessment of the evidence in the light of recent discoveries. Biochem Pharmacol. 2000 Jan. 1; 59(1):13-23.

Demonté D, Quivy V, Colette Y, Van Lint C. Administration of HDAC inhibitors to reactivate HIV-1 expression in latent cellular reservoirs: implications for the development of therapeutic strategies. Biochem Pharmacol. 2004 Sep. 15; 68(6):1231-8.

Dokmanovic M, Clarke C, Marks P A. Histone deacetylase inhibitors: overview and perspectives. Mol Cancer Res. 2007 October; 5(10):981-9.

Duong, V.; Bret, C.; Altucci, L.; Mai, A.; Duraffourd, C.; Loubersac, J.; Harmand, P.; Bonnet, S.; Valente, S.; Maudelonde, T.; Cavaillès, V.; Boulle, N. Specific regulation and activity of class II histone deacetylases in human breast cancer cells. Mol. Cancer. Res. 2008, in press.

Garaci E, Palamara A T, Ciriolo M R, D'Agostini C, Abdel-Latif M S, Aquaro S, Lafavia E, Rotilio G. Intracellular GSH content and HIV replication in human macrophages. J Leukoc Biol. 1997 July; 62(1):54-9.

Hamer D H. Can HIV be Cured? Mechanisms of HIV persistence and strategies to combat it. Curr HIV Res. 2004 April; 2(2):99-111.

Hauschild A, Trefzer U, Garbe C, Kaehler K C, Ugurel S, Kiecker F, Eigentler T, Krissel H, Schott A, Schadendorf D. Multicenter phase II trial of the histone deacetylase inhibitor pyridylmethyl-N-{4-[(2-aminophenyl)-carbamoyl]-benzyl}-carbamate in pretreated metastatic melanoma. Melanoma Res. 2008 August; 18(4):274-8.

Hezareh M. Prostratin as a new therapeutic agent targeting HIV viral reservoirs. Drug News Perspect. 2005 October; 18(8):496-500.

Hulgan T, Morrow J, D'Aquila R T, Raffanti S, Morgan M, Rebeiro P, Haas D W. Oxidant stress is increased during treatment of human immunodeficiency virus infection. Clin Infect Dis. 2003 Dec. 15; 37(12):1711-7.

Illi, B.; Dello Russo, C.; Colussi, C.; Rosati, J.; Pallaoro, M.; Spallotta, F.; Rotili, D.; Valente, S.; Ragone, G.; Martelli, F.; Biglioli, P.; Steinkuhler, C.; Gallinari, P.; Mai, A.; Capogrossi, M. C.; Gaetano, C. Nitric oxide modulates chromatin folding in human endothelial cells via protein phosphatase 2A activation and class II histone deacetylases nuclear shuttling. Circ Res. 2008, 102, 51-58.

Inoue, S.; Mai, A.; Dyer, M. J. S.; Cohen, G. M. Inhibition of histone deacetylase class I but not class II is critical for the sensitization of leukemic cells to tumor necrosis factor-related apoptosis-inducing ligand-induced apoptosis. Cancer Res. 2006, 66, 6785-6792.

Jiang G, Espeseth A, Hazuda D J, Margolis D M. c-Myc and Sp1 contribute to proviral latency by recruiting histone deacetylase 1 to the human immunodeficiency virus type 1 promoter. J. Virol. 2007 October; 81(20):10914-23.

Khan N, Jeffers M, Kumar S, Hackett C, Boldog F, Khramtsov N, Qian X, Mills E, Berghs S C, Carey N, Finn P W, Collins L S, Tumber A, Ritchie J W, Jensen P B, Lichenstein H S, Sehested M.

Lacreta F P, Brennan J M, Hamilton T C, Ozols R F, O'Dwyer P J. Stereoselective pharmacokinetics of L-buthionine SR-sulfoximine in patients with cancer. Drug Metab Dispos. 1994 November-December; 22(6):835-42.

Lehrman G, Hogue I B, Palmer S, Jennings C, Spina C A, Wiegand A, Landay A L, Coombs R W, Richman D D, Mellors J W, Coffin J M, Bosch R J, Margolis D M. Depletion of latent HIV-1 infection in vivo: a proof-of-concept study. Lancet. 2005 Aug. 13-19; 366(9485):523-4.

a Mai A, Massa S, Ragno R, Cerbara I, Jesacher F, Loidl P, Brosch G. 3-(4-Aroyl-1-methyl-1H-2-pyrrolyl)-N-hydroxy-2-alkylamides as a new class of synthetic histone deacetylase inhibitors. 1. Design, synthesis, biological evaluation, and binding mode studies performed through three different docking procedures. J Med. Chem. 2003 Feb. 13; 46(4):512-24.

b Mai, A.; Massa, S.; Pezzi, R.; Rotili, D.; Loidl, P.; Brosch, G. Discovery of (aryloxopropenyl)pyrrolyl hydroxyamides as selective inhibitors of class IIa histone deacetylase homologue HD1-A. J. Med. Chem. 2003, 46, 4826-4829.

a Mai, A.; Massa, S.; Pezzi, R.; Simeoni, S.; Rotili, D.; Nebbioso, A.; Scognamiglio, A.; Altucci, L.; Loidl, P.; Brosch, G. Class II (IIa)-selective histone deacetylase inhibitors. 1. Synthesis and biological evaluation of novel (aryloxopropenyl)pyrrolyl hydroxyamides. J. Med. Chem. 2005, 48, 3344-3353.

b Mai, A.; Massa, S.; Rotili, D.; Pezzi, R.; Bottoni, P.; Scatena, R.; Meraner, J.; Brosch, G. Exploring the connection unit in the HDAC inhibitor pharmacophore model: novel uracil-based hydroxamates. Bioorg. Med. Chem. Lett. 2005, 15, 4656-4661.

Mai A, Massa S, Rotili D, Simeoni S, Ragno R, Botta G, Nebbioso A, Miceli M, Altucci L, Brosch G. Synthesis and biological properties of novel, uracil-containing histone deacetylase inhibitors. J Med. Chem. 2006 Oct. 5; 49(20): 6046-56.

Mai A, Perrone A, Nebbioso A, Rotili D, Valente S, Tardugno M, Massa S, De Bellis F, Altucci L. Novel uracil-based 2-aminoanilide and 2-aminoanilide-like derivatives: histone deacetylase inhibition and in-cell activities. Bioorg Med Chem. Lett. 2008 Apr. 15; 18(8):2530-5.

Mottet D, Castronovo V. Histone deacetylases: a new class of efficient anti-tumor drugs. Med Sci (Paris). 2008 August-September; 24(8-9):742-6.

Munier S, Delcroix-Genête D, Carthagéna L, Gumez A, Hazan U. Characterization of two candidate genes, NCoA3 and IRF8, potentially involved in the control of HIV-1 latency. Retrovirology. 2005 Nov. 23; 2:73.

Nishioka C, Ikezoe T, Yang J, Takeuchi S, Koeffler H P, Yokoyama A. MS-275, a novel histone deacetylase inhibitor with selectivity against HDAC1, induces degradation of FLT3 via inhibition of chaperone function of heat shock protein 90 in AML cells. Leuk Res. 2008 September; 32(9):1382-92.

Palamara A T, Garaci E, Rotilio G, Ciriolo M R, Casabianca A, Fraternale A, Rossi L, Schiavano G F, Chiarantini L, Magnani M. Inhibition of murine AIDS by reduced glutathione. AIDS Res Hum Retroviruses. 1996 Sep. 20; 12(14):1373-81.

Ragno R, Simeoni S, Rotili D, Caroli A, Botta G, Brosch G, Massa S, Mai A. Class II-selective histone deacetylase inhibitors. Part 2: alignment-independent GRIND 3-D QSAR, homology and docking studies. Eur J Med. Chem. 2008 March; 43(3):621-32.

Saari H, Suomalainen K, Lindy O, Konttinen Y T, Sorsa T. Activation of latent human neutrophil collagenase by reactive oxygen species and serine proteases. Biochem Biophys Res Commun. 1990 Sep. 28; 171(3):979-87.

Sannella A R, Casini A, Gabbiani C, Messori L, Bilia A R, Vincieri F F, Majori G, Severini C. New uses for old drugs. Auranofin, a clinically established antiarthritic metallodrug, exhibits potent antimalarial effects in vitro: Mechanistic and pharmacological implications. FEBS Lett. 2008 Mar. 19; 582(6):844-7.

Savarino A, Pescarmona G P, Boelaert J R. Iron metabolism and HIV infection: reciprocal interactions with potentially harmful consequences? Cell Biochem Funct. 1999 December; 17(4):279-87.

Savarino A, Pistello M, D'Ostilio D, Zabogli E, Taglia F, Mancini F, Ferro S, Matteucci D, De Luca L, Barreca M L, Ciervo A, Chimirri A, Ciccozzi M, Bendinelli M. Human immunodeficiency virus integrase inhibitors efficiently suppress feline immunodeficiency virus replication in vitro and provide a rationale to redesign antiretroviral treatment for feline AIDS. Retrovirology. 2007 Oct. 30; 4:79.

Scognamiglio, A., Nebbioso, A., Manzo, F., Valente, S., Mai, A., Altucci, L. HDAC-class II specific inhibition involves HDAC proteasome-dependent degradation mediated by RANBP2. Biochim Biophys Acta 2008 released on web 2008 Jul. 22.

Smith S M. Valproic acid and HIV-1 latency: beyond the sound bite. Retrovirology. 2005 Sep. 19; 2:56.

Williams S A, Chen L F, Kwon H, Ruiz-Jarabo C M, Verdin E, Greene W C. NF-kappaB p50 promotes HIV latency through HDAC recruitment and repression of transcriptional initiation. EMBO J. 2006 Jan. 11; 25(1):139-49.

Zhao M, Rudek M A, Mnasakanyan A, Hartke C, Pili R, Baker S D. A liquid chromatography/tandem mass spectrometry assay to quantitate MS-275 in human plasma. J Pharm Biomed Anal. 2007 Jan. 17; 43(2):784-7.

EXAMPLE 3

Further Work on HDACI's+BSO

To investigate the cellular basis of the synergism between HDACi and BSO, we used the Jurkat model for HIV-1 quiescence. These results are derived from the A1 Jurkat cell clone, which has an integrated GFP/Tat construct under control of the HIV-1 LTR, which is quiescent in the majority of cells and thus allows us to examine, by flow cytometry, activation of the LTR promoter at a single-cell level [Jordan A, et al 2003]. Our results showed that BSO recruited HDACi-insensitive cells into the responding cell population (FIG. 13). Differently from the results obtained from p24 measurements in ACH-2 and U1 cells, BSO alone induced LTR activation in a small proportion of cells.

HIV-1 replicating cell cultures display decreased levels of reduced glutathione [Simon G, et al 1994]. We compared the toxicity of the BSO+HDACi combination in uninfected and latently infected cell lines. Results showed that, using BSO in combination with HDAC is, there was marked cytotoxicity at 72 h of incubation in latently infected but not in uninfected cell cultures (FIG. 14).

This is supported by experiments in uninfected Jurkat cells and Jurkat cell clones (6.3 and 8.4), which contain a quiescent HIV-1 genome (with the GFP gene) under control of the LTR [Jordan A, 2003, infra]. We found that the 6.3 cell clone succumbed more readily to the MS-275/BSO combination than its uninfected counterpart (FIG. 14). Similar results were obtained with the 8.4 clone (data not shown).

In conclusion, the effects of BSO allow us to amplify the proportion of cells responding to an HDACi-based HIV-1 reactivating treatment. In general, oxidative stress tilts the balance of HAT/HDAC activity towards increased HAT activity and DNA unwinding, thus facilitating the binding of several transcription factors [Rahman I, at al 2004]. This suggests important clinical uses, because a variegated phenotype after activation, with only a fraction of the cell population becoming activated in response to a global signal, was also shown by Jordan et al., 2004 [infra], who attributed this phenomenon to the different local chromatin environments.

Apart from amplifying the effect of histone deacetylase inhibitors, the results of the present study allow us to hypothesise that our strategy using pro-oxidant agents such as BSO in combination with HDAC is able to induce selective killing of the latently infected cells. This strategy can be considered to be one of the long-sought "shock and kill" strategies. These strategies consist of inducing, through drugs, HIV-1 activation from quiescence (i.e. the "shock" phase), in the presence of ART (to block viral spread), followed by the elimination of infected cells (i.e. the "kill" phase), through either natural means (e.g. immune response, viral cytopathogenicity) or artificial means (e.g. drugs, monoclonal antibodies, etc.) [Hamer D H, 2004]. Indeed, our strategy is based on an HDACi, which activates HIV-1 replication in latently infected cells (i.e. the "shock" phase), in combination with a pro-oxidant agent such as BSO, which amplifies the cellular damage due to the HIV-1 induced decay in the intracellular levels of reduced glutathione (i.e. the "kill" phase). The search of a drug combination capable of exerting such effects has, so far, been a "Holy Grail" in AIDS research.

REFERENCES FOR EXAMPLE 3

Jordan A, Bisgrove D, Verdin E: HIV reproducibly establishes a latent infection after acute infection of T cells in vitro. *EMBO J.* 2003, 22:1868-1877.

Simon G, Moog C, Obert G: Valproic acid reduces the intracellular level of glutathione and stimulates human immunodeficiency virus. *Chem Biol Interact* 1994, 91:111-121.

Rahman I, Marwick J, Kirkham P: Redox modulation of chromatin remodeling: impact on histone acetylation and deacetylation, NF-kappaB and pro-inflammatory gene expression. *Biochem Pharmacol* 2004, 68:1255-1267.

Hamer D H: Can HIV be Cured? Mechanisms of HIV persistence and strategies to combat it. *Curr HIV Res* 2004, 2:99-111.

EXAMPLE 4

Arsenic Trioxide

Gold salts and arsenicals share a number of biological effects, and are now showing new promise as potentially promising epigenetic metallodrugs with several applications in medicine. Their therapeutic use in other disease conditions has an ancient tradition, of course. Although arsenic is considered to be an element displaying both metal and non-metal properties, it behaves as a metal in many aspects. In its most common elemental form (gray arsenic), it has a metal-like nature and conducts electricity. Similar to gold salts, arsenicals have been employed therapeutically since the 5th century BC. Hippocrates used realgar ($As_2S_2$) and orpiment ($As_2S_3$) as remedies for ulcers. Traditional Chinese medicine used arsenicals, in combination with gold to treat various conditions. Olympiodorus of Thebes (5th century AD) roasted arsenic sulfide and obtained white arsenic ($As_2O_3$, but may also be found as $As_4O_6$). Both gold salts and arsenicals later found, among other uses, antirheumatic, antisyphilitic and antitumour applications [see Eisler, 2003, Giordano, 1844, Christison and Griffith, 1848, Cutler and Bradford, 1878, Waxman et al., 2001, Park et al., 2008]. Arsenic is also known as a poison, when used at higher dosage.

The use of arsenic trioxide and gold salts was gradually abandoned in the past century, limiting the use of arsenic trioxide to chronic promyelocytic leukemia and gold salts to rheumatoid arthritis. In the last decade, however, interest for these types of drugs has been refuelled in light of the discovery of their epigenetic effects, i.e. the capacity to induce modifications of the DNA structure without altering the sequence of bases. Structural modifications of DNA such as winding/unwinding regulate gene expression. Further research showed that arsenic trioxide and gold salts share important similarities in their effects at the cellular level, which might account for the similar therapeutic applications that both types of drugs have found during their history. Both arsenic trioxide and gold salts induce reactive oxygen species (ROS).

Oxidative stress is known to tilt the balance of HAT/HDAC activity towards increased HAT activity and DNA unwinding, thus facilitating the binding of several transcription factors [Rahman et al., 2004]. Interestingly, both arsenic trioxide and gold-containing compounds inhibit thioredoxin reductase and act as superoxide dismutase (SOD) mimics. Therefore, in light of these effects, and common epigenetic effects such as induction of HAT activity, gold compounds and arsenicals are starting to be considered as a unique drug class [Talbot et al., 2008].

This drug class, comprising arsenicals and gold-containing compounds, will be henceforth dubbed "epigenetic metallodrugs" i.e. metallodrugs having epigenetic effects. Other metallodrugs known to activate HIV-1 from latency, such as iron-containing compounds and cisplatin [Savarino et al., 1998; Spandidos et al., 1990], do not show the pro-differentiating effects of gold compounds and arsenicals.

Moreover, gold and arsenic ions share the ability to block the active site of thioredoxin reductases (TrxR) by complexing directly with the selenocystein residue important for the reducing activity of these proteins. This activity of auranofin is shared with arsenic trioxide [Liu et al. 2007]. The gold(I) derivatives and arsenic trioxide appear as very good inhibitors of thioredoxin reductase, exhibiting $IC_{50}$ values in the nanomolar range ($IC_{50}$<300 µM), whereas metal ions and metal complexes are active in the micromolar range (from 19 to 80 µM) [Bragadin et al., 2004; Lu et al., 2007]. Another activity shared by arsenic trioxide and a gold(I) derivative such as auranofin is the unique ability to suppress synthesis of TrxRs [Talbot et al., 2008].

We have shown in Example 1 that the gold-containing compound, auranofin is able to induce HIV-1 escape from latency in vitro at concentrations mimicking those found in plasma of humans with rheumatoid arthritis. If our theory is correct, the effects of the gold-containing compound auranofin on HIV-1 escape from latency should also be exerted by arsenicals.

Arsenic trioxide has well documented epigenetic potential, a well described toxicity profile and its clinical use is relatively safe at certain dosages.

We first tested the response to arsenic trioxide in Jurkat cell clones with an integrated green fluorescent protein (GFP)-encoding gene under control of the HIV-1 LTR [Jordan et al., 2003].

The experiments were conducted according to the techniques extensively described Example 1. In these Jurkat cell clones, GFP induction by HDACIs was evident only in a fraction of cells and increased in response to arsenic trioxide in a concentration-dependent manner (FIG. 15).

To evaluate the response to arsenic trioxide within a cellular population containing the entire HIV-1 genome, we used the latently infected T-lymphoid Jurkat cell clones 6.3 and 8.4, established by Jordan et al. [Jordan et al., 2003]. This cell clones contain the entire HIV-1 genome under control of the LTR and presenting the GFP gene replacing nef. As opposed to U1 cells, these cells display non-significant basal levels of HIV-1 expression and have a functional Tat/TAR axis. In the 8.4 cells, arsenic trioxide induced a dose-dependent shift in fluorescence (data not shown), which was evident mostly at the highest concentrations adopted.

We conclude that the effect of arsenic trioxide replicate those of auranofin in cell line models for HIV-1 latency. Similar to auranofin, cisplatin was capable of activating latent HIV-1 at concentrations in the nanomolar range. Auranofin and arsenic trioxide do not share their effects with other metallodrugs such as cisplatin, which activates quiescent HIV-1 in the micromolar rather than in the nanomolar range of concentrations [Spandidos et al., 1990]. Our results thus support the view that gold(I) derivatives and arsenic trioxide should be regarded as belonging to a unique drug class of epigenetic modulators. Similar to auranofin, arsenic trioxide might find an application in "smoking out" strategies to purge HIV-1 from reservoirs.

We have shown in Examples 2 and 3 that a "shock and kill" effect can be obtained in cell line models for HIV-1 latency by combining Class I histone deacetylase inhibitors (HDACIs) with buthionine sulfoximine, an inhibitor of gamma-glutamyl cysteine synthetase, i.e. a limiting enzyme for glutathione synthesis [Savarino et al., 2009].

Glutatione is undoubtedly one important antioxidant defense, however, BSO alone was incapable to induce HIV-1 escape from latency only poorly. This is likely to be explained by the fact that BSO does not per se cause an oxidative stress but, rather, impairs the ability of a cell population to counteract the oxidative stress induced by HDACIs [Palamara et al., unpublished data]. In this context, auranofin and arsenic trioxide are per se capable of inducing oxidative stress likely through their superoxide-dismutase mimicking effects and capable of counteracting the antioxidant defense by inhibiting TrxRs. These effects could represent a step forward in the exploitation of oxidative stress as a means to combat HIV-1 latency.

Recently, Chomont et al. identified transitional memory T-CD4+ cells ($T_{TM}$s) as the principal reservoir for HIV-1 latency in individuals under antiretroviral therapy (ART) and presenting low CD4 counts [Chomont et al., 2009]. $T_{TM}$s are precursors of central memory T CD4+ cells ($T_{CM}$s), which represent a more stable HIV-1 reservoir and survive for years. As compared to $T_{CM}$s, $T_{TM}$s present a less differentiated phenotype and proliferate in response to IL-7, a cytokine inducing stem cell proliferation. In order to obtain HIV-1 eradication from ART-treated individuals with low CD4 counts, Chomont et al. advocate treatment with an "intelligent-targeted chemotherapy", which, in combination with ART, be able to inhibit T-cell proliferation and decrease stem cell-ness in order to avoid generation of the long lasting $T_{CM}$ reservoir. The authors however were unable to identify suitable drug candidates. However, the HIV-1 inducing effects of arsenic trioxide (allowing elimination of the infected cells by viral cytopathogenicity or the immune system), added to its well-known antiblastic effects on lymphocytes as well as its marked pro-differentiating activity would make this drug an ideal candidate for clinical trials of HIV-1 eradication.

REFERENCES FOR EXAMPLE 4

Bragadin M, Scutari G, Folda A, Bindoli A, Rigobello M P. Effect of metal complexes on thioredoxin reductase and the regulation of mitochondrial permeability conditions. Ann N Y Acad. Sci. 2004 December; 1030:348-54.

Chomont N, El-Far M, Ancuta P, Trautmann L, Procopio F A, Yassine-Diab B, Boucher G, Boulassel M R, Ghattas G, Brenchley J M, Schacker T W, Hill B J, Douek D C, Routy J P, Haddad E K, Sékaly RP. HIV reservoir size and persistence are driven by T cell survival and homeostatic proliferation. Nat. Med. 2009 August; 15(8):893-900.

Cutler E G, Bradford E H. Action of iron, cod-lived oil and arsenic on the globular richness of the blood. Am J Med Sci 1878; 75:74-84.

Christison and Griffith's Dispensatory 1848 (A Dispensatory or Commentary on the Pharmacopeias of Great Britain and the United States). Lea and Blanchard publishers of Philadelphia.

Eisler R. Chrysotherapy: a synoptic review. Inflamm Res. 2003 December; 52(12):487-501.

Giordano A. Farmacologia, ossia trattato di farmacia teorico e pratico. Torino, 1844 Ed. Zecchi e Bona, Contrada Carlo Alberto.

Jordan A, Bisgrove D, Verdin E. HIV reproducibly establishes a latent infection after acute infection of T cells in vitro. *EMBO J.* 2003; 22:1868-1877.

Lu J, Chew E H, Holmgren A. Targeting thioredoxin reductase is a basis for cancer therapy by arsenic trioxide. Proc Natl Acad Sci USA. 2007 Jul. 24; 104(30):12288-93.

Park S J, Kim M, Kim N H, Oh M K, Cho J K, Jin J Y, Kim I S. Auranofin promotes retinoic acid- or dihydroxyvitamin D3-mediated cell differentiation of promyelocytic leukaemia cells by increasing histone acetylation. Br J. Pharmacol. 2008 July; 154(6):1196-205.

Rahman I, Marwick J, Kirkham P: Redox modulation of chromatin remodelling: impact on histone acetylation and deacetylation, NF-kappaB and pro-inflammatory gene expression. *Biochem Pharmacol* 2004, 68:1255-1267

Savarino A, Mai A, Norelli S, El Daker S, Valente S, Rotili D, Altucci L, Palamara A T, Garaci E. "Shock and kill" effects of class I-selective histone deacetylase inhibitors in combination with the glutathione synthesis inhibitor buthionine sulfoximine in cell line models for HIV-1 quiescence. Retrovirology. 2009 Jun. 2; 6:52.

Spandidos D A, Zoumpourlis V, Kotsinas A, Maurer H R, Patsilinacos P. Transcriptional activation of the human immunodeficiency virus long terminal repeat sequences by cis-platin. Genet Anal Tech Appl. 1990 September; 7(5): 138-41.

Talbot S, Nelson R, Self W T. Arsenic trioxide and auranofin inhibit selenoprotein synthesis: implications for chemotherapy for acute promyelocytic leukaemia. Br J. Pharmacol. 2008 July; 154(5):940-8.

Waxman S, Anderson K C. History of the development of arsenic derivatives in cancer therapy. The Oncologist, Vol. 6, Suppl 2, 3-10, April 2001.

The invention claimed is:

1. A method for selectively targeting a cell latently infected with human immunodeficiency virus (HIV), which method comprises contacting a cell with auranofin in an amount effective for inducing replication of the latent HIV, wherein the auranofin has an epigenetic effect on the latently infected cell.

2. A method according to claim 1, in which the auranofin is administered in combination with at least one compound selected from the group consisting of: a histone deacetylase inhibitor (HDACI), suberoylanilide hydroxamic acid (SAHA), butionine sulfoximine (BSO), iron nitriloacetate (FeNTA), and ferrous sulphate.

3. A method according to claim 1, in which the cell is selected from the group consisting of an ACH-2 cell and a U1 cell.

4. A method according to claim 1, additionally comprising administration of a conventional anti-retroviral therapy.

5. A method for treating a retroviral infection in an individual, which method comprises administering, to the individual, auranofin in an amount effective for inducing replication of latent HIV, wherein the auranofin has an epigenetic effect.

6. A method according to claim 5, wherein the auranofin is administered in combination with at least one compound selected from the group consisting of: a histone deacetylase inhibitor (HDCAI), suberoylanilide hydroxamic acid (SAHA), butionine sulfoximine (BSO), iron nitriloacetate (FeNTA) and ferrous sulphate.

7. A method according to claim 5, additionally comprising administration of a conventional anti-retroviral therapy.

8. A method according to claim 5, wherein the auranofin is administered in combination with suberoylanilide hydroxamic acid (SAHA).

* * * * *